United States Patent
Gu et al.

(10) Patent No.: US 11,096,893 B2
(45) Date of Patent: Aug. 24, 2021

(54) GLUCOSE SENSITIVE COMPOSITIONS FOR DRUG DELIVERY

(71) Applicant: NORTH CAROLINA STATE UNIVERSITY, Raleigh, NC (US)

(72) Inventors: Zhen Gu, Los Angeles, CA (US); Jicheng Yu, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 16/618,547

(22) PCT Filed: Jun. 4, 2018

(86) PCT No.: PCT/US2018/035799
§ 371 (c)(1),
(2) Date: Dec. 2, 2019

(87) PCT Pub. No.: WO2018/223114
PCT Pub. Date: Dec. 6, 2018

(65) Prior Publication Data
US 2020/0085743 A1    Mar. 19, 2020

Related U.S. Application Data

(60) Provisional application No. 62/514,099, filed on Jun. 2, 2017.

(51) Int. Cl.
*A61K 9/127* (2006.01)
*A61P 3/10* (2006.01)
(Continued)

(52) U.S. Cl.
CPC .......... *A61K 9/1271* (2013.01); *A61K 9/4816* (2013.01); *A61K 38/28* (2013.01);
(Continued)

(58) Field of Classification Search
CPC .... A61K 9/1271; A61K 9/4816; A61K 38/28; A61K 47/24; A61K 47/36; A61K 9/127;
(Continued)

(56) References Cited

U.S. PATENT DOCUMENTS

| 5,478,575 A | 12/1995 | Miyazaki et al. |
| 2010/0029545 A1 | 2/2010 | Sumerlin et al. |

(Continued)

FOREIGN PATENT DOCUMENTS

| WO | 2016076317 A1 | 5/2016 |
| WO | 2006102762 A1 | 10/2016 |
| WO | 2016172320 A1 | 10/2016 |

OTHER PUBLICATIONS

DasGupta, I., et al in PLoS One, vol. 7 (1), pp. 1-21, 2012.*
(Continued)

*Primary Examiner* — Gollamudi S Kishore
(74) *Attorney, Agent, or Firm* — Meunier Carlin & Curfman LLC

(57) ABSTRACT

Disclosed herein are glucose-sensitive drug delivery systems including polymeric shell encapsulating an active agent. Upon exposure to a sufficient concentration of glucose, the shell is ruptured, releasing the active agent for absorption.

20 Claims, 6 Drawing Sheets

(51) Int. Cl.
  *A61K 9/48* (2006.01)
  *A61K 38/28* (2006.01)
  *A61K 47/24* (2006.01)
  *A61K 47/36* (2006.01)
(52) U.S. Cl.
  CPC .................................. *A61K 47/24* (2013.01); *A61K 47/36* (2013.01); *A61P 3/10* (2018.01)
(58) Field of Classification Search
  CPC .......................... A61K 9/5031; A61K 9/5146; A61K 47/6911; A61P 3/10
  See application file for complete search history.

(56) References Cited

U.S. PATENT DOCUMENTS

| | | | | |
|---|---|---|---|---|
| 2011/0177155 | A1* | 7/2011 | Peer | A61K 45/06 424/450 |
| 2013/0110040 | A1 | 5/2013 | Serpe | |
| 2014/0227349 | A1* | 8/2014 | Annapragada | A61K 38/28 424/450 |
| 2014/0369935 | A1* | 12/2014 | Okamoto | A61K 31/675 424/9.6 |
| 2015/0283247 | A1* | 10/2015 | Auzely-Velty | A61P 3/10 514/5.9 |

OTHER PUBLICATIONS

Asjley, J.D., et al ub J. Med. Chem, 57 (12), pp. 5282-5292, 2014.*
International Search Report and Written Opinion issued in corresponding PCT Application No. PCT/US/2018/035799, dated Aug. 31, 2018, 9 pages.
Tang, et al. "Contraction-type glucose-sensitive microgel functionalized with a 2-substituted phenylboronic acid ligand," Polym. Chem. 2014, vol. 5, pp. 1782-1790.
Kim, Sung Han, Insik In, and Sung Young Park. "pH-responsive NIR-absorbing fluorescent polydopamine with hyaluronic acid for dual targeting and synergistic effects of photothermal and chemotherapy." Biomacromolecules 18.6 (2017): 1825-1835.
Jo, M., eet al., "Preparation and Characterization of Glucose-Responsive Hyaluronate-Based Nanoparticles", Tissue Eng., Part A., vol. 21, 2015, p. S-362.
Brooks, William LA, and Brent S. Sumerlin. "Synthesis and applications of boronic acid-containing polymers: from materials to medicine." Chemical reviews 116.3 (2016): 1375-1397.
Tarus, Dominte, et al. "Readily Prepared Dynamic Hydrogels by Combining Phenyl Boronic Acid-and Maltose-Modified Anionic Polysaccharides at Neutral pH." Macromolecular rapid communications 35.24 (2014): 2089-2095.
Ma, Rujiang, et al. "Phenylboronic acid-based complex micelles with enhanced glucose-responsiveness at physiological pH by complexation with glycopolymer." Biomacromolecules 13.10 (2012): 3409-3417.
Matsumoto, Akira, Ryo Yoshida, and Kazunori Kataoka. "Glucose-responsive polymer gel bearing phenylborate derivative as a glucose-sensing moiety operating at the physiological pH." Biomacromolecules 53 (2004): 1038-1045.
Wu, Zhongming, et al. "Phenylboronic acid grafted chitosan as a glucose-sensitive vehicle for controlled insulin release." Journal of pharmaceutical sciences 100.6 (2011): 2278-2286.
Serre, Karine, et al. "Efficient presentation of multivalent antigens targeted to various cell surface molecules of dendritic cells and surface lg of antigen-specific B cells." The Journal of Immunology 161.11 (1998): 6059-6067.
Extended Search Report issued for Application No. 18810805.4, dated Feb. 8, 2021.

* cited by examiner

GLUCOSE SENSITIVE COMPOSITIONS FOR DRUG DELIVERY

CROSS REFERENCE TO RELATED APPLICATION

This application claims priority to PCT International Application No. PCT/US2018/035799, filed Jun. 4, 2018, which claims the benefit of U.S. Provisional Application 62/514,099, filed on Jun. 2, 2017, the contents of which are each hereby incorporated in their entirety.

STATEMENT OF GOVERNMENT SUPPORT

This invention was made with government support under grant number TR001111 awarded by the National Institutes of Health. The government has certain rights to this invention.

FIELD OF THE INVENTION

This application is directed to glucose-sensitive orally administrable compositions.

BACKGROUND

The worldwide increase in the prevalence of diabetes mellitus is a serious public health burden. The medical management of diabetes centers around achieving tight control of blood glucose levels to prevent the long-term organ damage that is associated with chronic hyperglycemia. To this end, patients self-administer insulin in a daily regimen that commonly involves subcutaneous injection of commercial insulin formulations. For example, rapid-acting insulin is dosed according to carbohydrate content and subcutaneously injected just before or after each meal to mitigate postprandial glycemic excursions. Current standards of care for diabetes self-management recommend that patients quantify carbohydrate for each meal and dose insulin accordingly. However, the efficacy of this method is limited by human error in counting or calculation, the complex influence of other dietary components or lifestyle factors, and poor patient adherence, leading to inadequate control of postprandial glucose levels. Moreover, the injection of insulin is associated with a high degree of human error and poor patient compliance, as well as complications such as pain, tissue invasion, infection, and nerve damage.

To improve quality of life for patients with diabetes, recent efforts in the past decades have focused on developing alternative strategies based on oral, nasal, pulmonary, and transdermal delivery routes. Oral insulin delivery has emerged as one of the most convenient administration routes, and numerous insulin formulation have been developed to enhance oral insulin delivery efficiency by improving intestinal absorption and preventing insulin digestion. However, current formulations cannot address the need to release of insulin specifically following meals, where an optimized oral insulin delivery system would supply insulin to the body at a time when it is needed.

There remains a need for improved orally administrable compositions for biological agents such as insulin. There remains a need for improved methods of treating diabetes and related disorders that do not require patients to quantitate food intake. There remains a need for orally administrable compositions that selectively release a therapeutic agent after food digestion. There remains a need for an oral insulin delivery method that can respond to the elevated intestinal glucose levels following digestion of a meal, thereby mitigating the need for patients to count carbohydrates and dose insulin.

SUMMARY OF THE INVENTION

Disclosed herein are oral drug delivery systems including a glucose-responsive boronic ester polymer conjugate encapsulating an active agent. In the presence of elevated glucose levels, the boronic ester is cleaved and the polymer shell is ruptured, releasing its contents. The systems can include a liposome loaded with a therapeutic agent such as insulin. The systems can include one or more targeting moieties to facility delivery of the agent to a desired location along the intestinal track.

DETAILED DESCRIPTION

Figure 1:
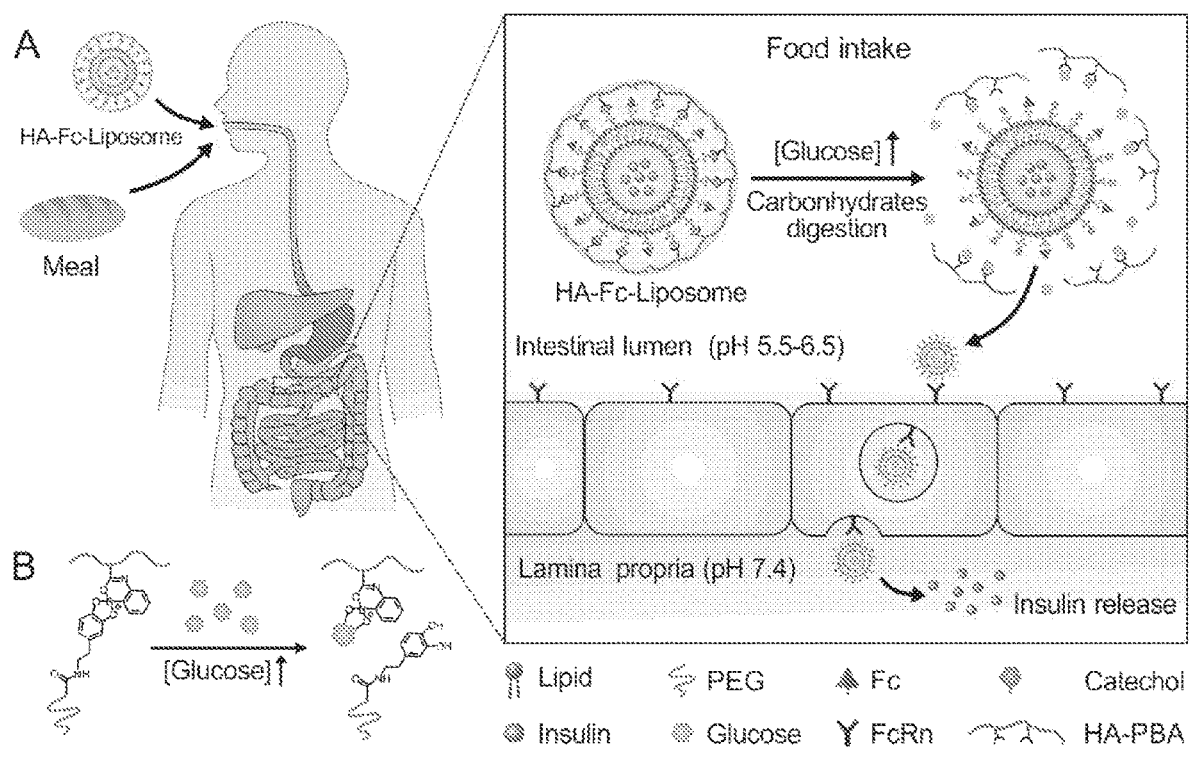
FIG. 1 includes a schematic of the glucose-responsive oral insulin delivery system with glucose-sensitive HA shell for postprandial glycemic regulation. (A) Schematic of insulin-loaded liposomes with glucose-responsive detachable HA shell for oral insulin delivery triggered by an evaluated glucose concentration in the intestine after meals. (B) Schematic of formation and response mechanism of glucose-responsive HA shell.

Before the present methods and systems are disclosed and described, it is to be understood that the methods and systems are not limited to specific synthetic methods, specific components, or to particular compositions. It is also to be understood that the terminology used herein is for the purpose of describing particular embodiments only and is not intended to be limiting.

As used in the specification and the appended claims, the singular forms "a," "an" and "the" include plural referents unless the context clearly dictates otherwise. Ranges may be expressed herein as from "about" one particular value, and/or to "about" another particular value. When such a range is expressed, another embodiment includes¬ from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other additives, components, integers or steps. "Exemplary" means "an example of" and is not intended to convey an indication of a preferred or ideal embodiment. "Such as" is not used in a restrictive sense, but for explanatory purposes.

Pharmaceutically acceptable salts are salts that retain the desired biological activity of the parent compound and do not impart undesirable toxicological effects. Examples of such salts are acid addition salts formed with inorganic acids, for example, hydrochloric, hydrobromic, sulfuric, phosphoric, and nitric acids and the like; salts formed with organic acids such as acetic, oxalic, tartaric, succinic, maleic, fumaric, gluconic, citric, malic, methanesulfonic, p-toluenesulfonic, napthalenesulfonic, and polygalacturonic acids, and the like; salts formed from elemental anions such as chloride, bromide, and iodide; salts formed from metal hydroxides, for example, sodium hydroxide, potassium hydroxide, calcium hydroxide, lithium hydroxide, and magnesium hydroxide; salts formed from metal carbonates, for example, sodium carbonate, potassium carbonate, calcium carbonate, and magnesium carbonate; salts formed from metal bicarbonates, for example, sodium bicarbonate and potassium bicarbonate; salts formed from metal sulfates, for example, sodium sulfate and potassium sulfate; and salts formed from metal nitrates, for example, sodium nitrate and potassium nitrate. Pharmaceutically acceptable and non-pharmaceutically acceptable salts may be prepared using procedures well known in the art, for example, by reacting a sufficiently basic compound such as an amine with a suitable acid comprising a physiologically acceptable anion. Alkali metal (for example, sodium, potassium, or lithium) or alkaline earth metal (for example, calcium) salts of carboxylic acids can also be made.

The term "alkyl" as used herein is a branched or unbranched hydrocarbon group such as methyl, ethyl, n-propyl, isopropyl, n-butyl, isobutyl, t-butyl, pentyl, hexyl, heptyl, octyl, nonyl, decyl, dodecyl, and the like. The alkyl group can also be substituted or unsubstituted. Unless stated otherwise, the term "alkyl" contemplates both substituted and unsubstituted alkyl groups. The alkyl group can be substituted with one or more groups including, but not limited to, alkoxy, alkenyl, alkynyl, cycloalkyl, heterocycloalkyl, aryl, heteroaryl, aldehyde, amino, carboxylic acid, ester, ether, halide, hydroxy, ketone, nitro, silyl, sulfo-oxo, or thiol. An alkyl group which contains no double or triple carbon-carbon bonds is designated a saturated alkyl group, whereas an alkyl group having one or more such bonds is designated an unsaturated alkyl group. Unsaturated alkyl groups having a double bond can be designated alkenyl groups, and unsaturated alkyl groups having a triple bond can be designated alkynyl groups. Unless specified to the contrary, the term alkyl embraces both saturated and unsaturated groups.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, etc. The term "heterocycloalkyl" is a cycloalkyl group as defined above where at least one of the carbon atoms of the ring is replaced with a heteroatom such as, but not limited to, nitrogen, oxygen, sulfur, selenium or phosphorus. The cycloalkyl group and heterocycloalkyl group can be substituted or unsubstituted. Unless stated otherwise, the terms "cycloalkyl" and "heterocycloalkyl" contemplate both substituted and unsubstituted cyloalkyl and heterocycloalkyl groups. The cycloalkyl group and heterocycloalkyl group can be substituted with one or more groups including, but not limited to, alkyl, alkoxy, alkenyl, alkynyl, cycloalkyl, heterocycloalkyl, aryl, heteroaryl, aldehyde, amino, carboxylic acid, ester, ether, halide, hydroxy, ketone, nitro, silyl, sulfo-oxo, or thiol. A cycloalkyl group which contains no double or triple carbon-carbon bonds is designated a saturated cycloalkyl group, whereas an cycloalkyl group having one or more such bonds (yet is still not aromatic) is designated an unsaturated cycloalkyl group. Unless specified to the contrary, the term cycloalkyl embraces both saturated and unsaturated, non-aromatic, ring systems.

Unless stated to the contrary, a formula with chemical bonds shown only as solid lines and not as wedges or dashed lines contemplates each possible isomer, e.g., each enantiomer, diastereomer, and meso compound, and a mixture of isomers, such as a racemic or scalemic mixture. A compound depicted with wedges and dashed lines for bonds contemplates both the specifically depicted stereoisomer, as well the racemic mixture. The term "enantioenriched" means that the depicted enantiomer is present in a greater amount than the non-depicted enantiomer.

The term "aryl" as used herein is an aromatic ring composed of carbon atoms. Examples of aryl groups include, but are not limited to, phenyl and naphthyl, etc. The term "heteroaryl" is an aryl group as defined above where at least one of the carbon atoms of the ring is replaced with a heteroatom such as, but not limited to, nitrogen, oxygen, sulfur, selenium or phosphorus. The aryl group and heteroaryl group can be substituted or unsubstituted. Unless stated otherwise, the terms "aryl" and "heteroaryl" contemplate both substituted and unsubstituted aryl and heteroaryl groups. The aryl group and heteroaryl group can be substituted with one or more groups including, but not limited to, alkyl, alkoxy, alkenyl, alkynyl, cycloalkyl, heterocycloalkyl, aryl, heteroaryl, aldehyde, amino, carboxylic acid, ester, ether, halide, hydroxy, ketone, nitro, silyl, sulfo-oxo, or thiol.

Exemplary heteroaryl and heterocyclyl rings include: benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyL cirrnolinyl, decahydroquinolinyl, 2H,6H~1,5,2-dithiazinyl, dihydrofuro[2,3 b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, and xanthenyl.

The terms "alkoxy," "cycloalkoxy," "heterocycloalkoxy," "cycloalkoxy," "aryloxy," and "heteroaryloxy" have the aforementioned meanings for alkyl, cycloalkyl, heterocycloalkyl, aryl and heteroaryl, further providing said group is connected via an oxygen atom.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valencies of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. Unless specifically stated, a substituent that is said to be "substituted" is meant that the substituent can be substituted with one or more of the following: alkyl, alkoxy, alkenyl, alkynyl, cycloalkyl, heterocycloalkyl, aryl, heteroaryl, aldehyde, amino, carboxylic acid, ester, ether, halide, hydroxy, ketone, nitro, silyl, sulfo-oxo, or thiol.

Unless specified to the contrary, the terms "carboxylic acid" and "carboxylate" are used interchangeably. The skilled person appreciates that the functional group interchanges between the two forms depending on the pH of its local environment.

As used herein, "hyaluronic acid" includes both neutral and anionic (i.e., salt) forms of hyaluronic acid.

As used herein, the term "insulin" embraces all therapeutically acceptable forms of the agent, including regular insulin, insulin degludec, insulin lispro, insulin aspart, insulin glulisine, insulin detemir, insulin glargine, NPH insulin, animal insulin. Combinations of different insulin forms may also be used.

As used herein, and unless otherwise specified, "lipid" is understood to be a fatty acid, fatty acid salt, fatty alcohol, or phospholipid. Lipids include sphingolipids, including, but not limited to, sphingomyelin; glycosphingolipids including, but not limited to, gangliosides, globocides and cerebrosides; and surfactant amines including, but not limited to, stearyl, oleyl and linoleyl amines.

As used herein, and unless otherwise specified, "phospholipid" is understood to be an amphyphilic derivative of glycerol, in which one of its hydroxyl groups is esterified with phosphoric acid and the other two hydroxyl groups are esterified with long-chain fatty acids that can be equal to or different from each other and can be saturated or unsaturated. A neutral phospholipid is generally one in which the other phosphoric acid hydroxyl is esterified by an alcohol substituted by a polar group (usually hydroxyl or amino) and whose net charge is zero. A phospholipid with a charge is generally one in which the other phosphoric acid hydroxyl is esterified by an alcohol substituted by a polar group and whose net charge is positive or negative.

Disclosed are components that can be used to perform the disclosed methods and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all aspects of this application including, but not limited to, steps in disclosed methods. Thus, if there are a variety of additional steps that can be performed it is understood that each of these additional steps can be performed with any specific embodiment or combination of embodiments of the disclosed methods.

Disclosed herein are glucose-responsive compositions for oral drug delivery. The drug delivery system includes a core encapsulated by a polymeric shell. The therapeutic agent, contained within or on the core, is protected from the acidic conditions of the stomach by the polymeric shell. Upon entering the small intestine, where exposed to higher concentrations of glucose as well as different pH levels, the polymer shell disassociates from the core, releasing the therapeutic agent for absorption. The core can be encapsulated with the polymer via a boronate ester. In some embodiments, the core is encapsulated with the polymer via an aminoboronate ester formed between the polymer and a diol moiety present in the core.

The encapsulated core is released when the polymeric shell encounters a sufficiently glucose-rich environment. For instance, the shell can remain intact until the glucose concentration is at least 0.1 mM, at least 0.25 mM, at least 0.5 mM, at least 0.75 mM, at least 1 mM, at least 2.5 mM, or at least 5 mM.

The drug delivery system can include an aminoboronate ester, having the partial formula:

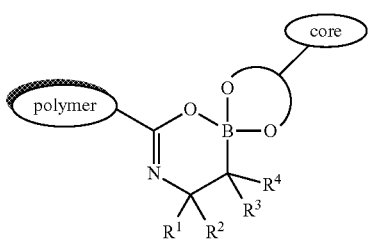

wherein $R^1$, $R^2$, $R^3$, and $R^4$ are independently selected from hydrogen, $C_{1-8}$ alkyl, $C_{2-8}$ alkenyl, $C_{2-8}$ alkynyl, aryl, heteroaryl, $C_{3-8}$ cycloalkyl, and $C_{1-8}$ heteroaryl, which may be substituted or unsubstituted, and wherein any two or more of $R^1$, $R^2$, $R^3$, and $R^4$ may together form a ring. In some embodiments, each of $R^1$ and $R^3$ are hydrogen and each of $R^2$ and $R^4$ are a non-hydrogen group, as defined above. For instance, $R^2$ and $R^4$ may together form a phenyl ring, and IV and $R^3$ are hydrogen. In another embodiment, each of $R^1$, $R^2$, $R^3$, and $R^4$ are methyl. In yet a further embodiment, each of $R^1$, $R^2$, $R^3$, and $R^4$ are hydrogen. In some embodiments, each of $R^2$, $R^3$, and $R^4$ are hydrogen and IV is $C_{1-8}$ alkyl group. In other embodiments, $R^3$ and $R^4$ are each hydrogen, and $R^1$ and $R^2$ are each independently $C_{1-8}$ alkyl groups and may together form a ring. In other cases, $R^1$ and $R^2$ are each hydrogen, and $R^3$ and $R^4$ are each independently $C_{1-8}$ alkyl groups and may together form a ring.

Generally, any biocompatible polymer may be used for the shell. It is preferred that the biocompatible polymer include a carboxylic acid moiety for ligating the boronic ester, however, other ligating modalities may also be employed. Exemplary polymers include hyaluronic acid, poly(γ-glutamic acid), poly(α-glutamic acid), poly(aspartic acid), chondroitin sulfate, carboxymethylcellulose, and combinations thereof. Polymers useful for the compositions can have a molecular weight of from 100,000-10,000,000, from 100,000-1,000,000, from 100,000-750,000, from 250,000-750,000, or from 200,000-500,000.

Hyaluronic acid is a preferred polymer for the shell. Hyaluronic acid polymers useful for the compositions can have a molecular weight of from 100,000-10,000,000, from 100,000-1,000,000, from 100,000-750,000, from 250,000-750,000, or from 200,000-500,000. Hyaluronic acid is a glycosaminoglycan consisting of repeating D-gluconic acid and N-acetyl-D-glucosamine disaccharide units:

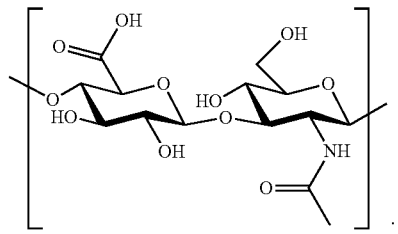

The carboxylic acid group in hyaluronic acid serves as the attachment point for the boronic ester. After incorporation, the hyaluronic acid will include subunits having the following formula:

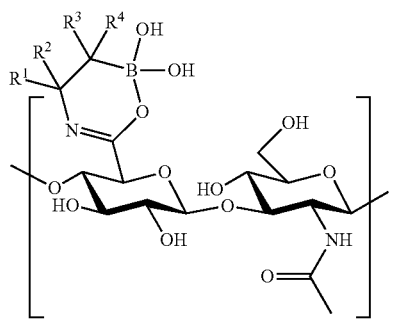

wherein $R^1$, $R^2$, $R^3$, and $R^4$ have the meanings given above. The skilled person will appreciate that other carboxylic acid containing polymers can be ligated to the boronic ester in similar fashion. The polymer/boronic ester can be characterized by the percentages of carboxylate moiety that have been modified to contain the boronic ester. In some embodiments, at least 2%, at least 4%, at least 6%, at least 8%, at least 10%, at least 12%, at least 14%, at least 16%, at least 18%, at least 20%, at least 25%, at least 30%, at least 35%, at least 40%, at least 45%, or at least 50% of the carboxylate groups are modified to contain the boronic ester. In some embodiments, at least 2%, at least 4%, at least 6%, at least 8%, at least 10%, at least 12%, at least 14%, at least 16%, at least 18%, at least 20%, at least 25%, at least 30%, at least 35%, at least 40%, at least 45%, or at least 50% of the subunits in the hyaluronic acid will be modified as depicted above. In other embodiments, from 2-50%, from 2-25%, from 2-20%, from 4-20%, from 6-20%, from 8-20%, from 10-20%, from 12-20%, from 14-20%, from 10-18%, from 10-16%, or from 12-16% of the carboxylate groups are modified to contain the boronic ester. In some embodiments, from 10-50%, from 15-50%, from 20-50%, from 25-50%, from 30-50%, from 40-50%, from 10-30%, from 15-30%, from 20-30%, from 25-30% of the carboxylate groups are modified to contain the boronic ester. In further embodiments, from 50-100%, from 50-90%, from 50-80%, from 50-70%, from 50-60%, from 60-100%, from 70-100%, from 80-100%, or from 90-100% of the carboxylate groups are modified to contain the boronic ester. In some preferred embodiments, from 10-20% or 12-16% of the carboxylate groups are modified to contain the boronic ester.

The boronic esters may be prepared from aminoboronic acids using conventional amide-forming techniques. The boronic acids have the general formula:

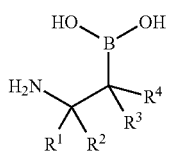

wherein $R^1$, $R^2$, $R^3$, and $R^4$ have the meanings given above. In some cases, the carboxylic acid groups in the polymer are be activated by the combination of 1-ethyl-3-(3-dimethylaminopropyl) carbodiimide (EDC) and N-hydroxysuccinimide (NHS) in water, and the boronic acid can then be added to the system. After the reaction is complete, the solvent can be removed by evaporation or lyophilization.

In certain embodiments, the core comprises a liposome, into which one or more therapeutic agents may be loaded. Suitable therapeutic agents that can be administered using the compositions include small molecule drugs and therapeutic proteins, including vaccines and monoclonal antibodies.

Exemplary classes of therapeutic proteins include antibody-based drugs, Fc fusion proteins, anticoagulants, blood factors, bone morphogenetic proteins, engineered protein scaffolds, enzymes, growth factors, hormones, interferons, interleukins, and thrombolytics. Exemplary therapeutic proteins include insulin, pramlintide, growth hormone somatotropin, mecasermin, Factor VIII, Factor IX, antithrombin III, protein C concentrate, glucocerebrosidase, alglucosidase, laronidase, idursulphase, galsulphase, agalsidase, α-1 proteinase inhibitor, lactase, pancreatic enzymes, adenosine deaminase, pooled immunoglobulins, human albumin, erythropoietin, darbepoetin, filgrastim, pegfilgrastim, sagramostim, oprelvekin, FSH, HCG, lutropin, interferon, aldesleukin, altephase, reteplase, tenecteplase, urokinase, Factor VIIa, drotrecogin, salmon calcitonin, teriparatide, exenatide, octreotide, dibotermin, human bone protein, histrelin, palifermin, becaplermin, trypsin, nesiritide, asparaginase, rasburicase, lepirudin, bivalirudin, streptokinase, and anistreplase. In particularly preferred embodiments, the therapeutic protein is insulin such as regular insulin, insulin degludec, insulin lispro, insulin aspart, insulin glulisine, insulin detemir, insulin glargine, NPH insulin, animal insulin, and combinations thereof.

The compositions disclosed herein may be used to treat a variety of glucose-implicated disorders. For instance, the compositions may be used to treat type 1 diabetes mellitus, type 2 diabetes mellitus, gestational diabetes, as well as other acute and chronic hyperglycemic disorders.

Exemplary small molecule drugs include anti-cancer agents. The compositions disclosed herein may be used to treat a variety of different cancers, including acute lymphoblastic leukemia (ALL), acute myeloid leukemia (AML), cancer in adrenocortical carcinoma, adrenal cortex cancer, AIDS-related cancers, Kaposi sarcoma, AIDS-related lymphoma, primary CNS lymphoma, anal cancer, appendix cancer, carcinoid tumors, astrocytomas, atypical teratoid/rhabdoid tumor, basal cell carcinoma, skin cancer (nonmelanoma), bile duct cancer, extrahepatic bladder cancer, bladder cancer, bone cancer (includes Ewing sarcoma and osteosarcoma and malignant fibrous histiocytoma), brain tumors, breast cancer, bronchial tumors, Burkitt lymphoma (non-Hodgkin), carcinoid tumor, cardiac (heart) tumors, atypical teratoid/rhabdoid tumor, embryonal tumors, germ cell tumors, lymphoma, primary-cervical cancer, cholangiocarcinoma, chordoma, chronic lymphocytic leukemia (CLL), chronic myelogenous leukemia (CML), chronic myeloproliferative neoplasms, colorectal cancer, colorectal cancer, craniopharyngioma, cutaneous T-cell lymphoma, ductal carcinoma in situ (DCIS), embryonal tumors, central nervous system, endometrial cancer, ependymoma, esophageal, esthesioneuroblastoma, ewing sarcoma, extracranial germ cell tumor, extragonadal germ cell tumor, eye cancer, intraocular melanoma, retinoblastoma, fallopian tube cancer, fibrous histiocytoma of bone, malignant, and osteosarcoma, gallbladder cancer, gastric (stomach) cancer, gastric (stomach) cancer, gastrointestinal carcinoid tumor, gastrointestinal stromal tumors (GIST), gastrointestinal stromal tumors (GIST), germ cell tumors, central nervous system, extracranial, extragonadal, ovarian testicular, gestational trophoblastic disease, gliomas, hairy cell leukemia, head and neck cancer, heart tumors, hepatocellular (liver) cancer, histiocytosis, Langerhans Cell, Hodgkin's lymphoma, hypopharyngeal cancer, intraocular melanoma, islet cell tumors, pancreatic neuroendocrine tumors, Kaposi sarcoma, kidney—langerhans cell histiocytosis, laryngeal cancer, laryngeal cancer and papillomatosis, leukemia, lip and oral cavity cancer, liver cancer (primary), lung cancer, lung cancer, lymphoma—macroglobulinemia, Waldenström—Non-Hodgkin lymphoma, male breast cancer, malignant fibrous histiocytoma of bone and osteosarcoma, melanoma, intraocular (eye), Merkel cell carcinoma, mesothelioma, malignant, mesothelioma, metastatic squamous neck cancer with occult primary, midline tract carcinoma involving NUT gene, mouth cancer, multiple endocrine neoplasia syndromes, multiple myeloma/plasma cell neoplasms, mycosis fungoides, myelodysplastic syndromes, myelodysplastic/myeloproliferative neoplasms and chronic myeloproliferative neoplasms, myelogenous leukemia, chronic (CML), myeloid leukemia, acute (AML), nasal cavity and paranasal sinus cancer, nasopharyngeal cancer, nasopharyngeal cancer, neuroblastoma, non-hodgkin lymphoma, non-small cell lung cancer, oral cancer, lip and oral cavity cancer and oropharyngeal cancer, osteosarcoma and malignant fibrous histiocytoma of bone, ovarian cancer, pancreatic cancer and pancreatic neuroendocrine tumors (islet cell tumors), papillomatosis, paraganglioma, paraganglioma, paranasal sinus and nasal cavity cancer, parathyroid cancer, penile cancer, pharyngeal cancer, pheochromocytoma, pheochromocytoma, pituitary tumor, plasma cell neoplasm/multiple myeloma, pleuropulmonary blastoma, pregnancy and breast cancer, primary central nervous system (CNS) lymphoma, primary peritoneal cancer, prostate cancer, rectal cancer, renal cell (kidney) cancer, retinoblastoma, rhabdomyosarcoma, salivary gland cancer, salivary gland tumors, Ewing sarcoma, Kaposi sarcoma, osteosarcoma, rhabdomyosarcoma, uterine sarcoma, vascular tumors, Sézary syndrome, skin cancer, small cell lung cancer, small intestine cancer, soft tissue sarcoma, squamous cell carcinoma, squamous neck cancer with occult primary, metastatic, stomach (gastric) cancer, stomach (gastric) cancer, T-cell lymphoma, cutaneous, testicular cancer, throat cancer, thymoma and thymic carcinoma, thyroid cancer, ureter and renal pelvis, transitional cell cancer, urethral cancer, uterine cancer, endometrial and uterine sarcoma, vaginal cancer, vaginal cancer, vascular tumors, vulvar cancer, Waldenström Macroglobulinemia, ad Wilms Tumor.

Exemplary anti-cancer agents that may be administered using the liposomes include Abiraterone, Methotrexate, Abraxane (Paclitaxel Albumin-stabilized Nanoparticle Formulation, Brentuximab Vedotin, Ado-Trastuzumab, Emtansine, Adriamycin, Afatinib, Everolimus, Akynzeo (Netupitant and Palonosetron Hydrochloride), Imiquimod, Aldesleukin, Alectinib, Alemtuzumab, Melphalan, Pemetrexed, Palonosetron, Chlorambucil, Aminolevulinic Acid, Anastrozole, Aprepitant, Pamidronate, Anastrozole, Exemestane, Nelarabine, Arsenic Trioxide, Ofatumumab, Asparaginase *Erwinia chrysanthemi*, Atezolizumab, Bevacizumab, Axitinib, Azacitidine, BEACOPP, Carmustine, Belinostat, Bendamustine, BEP, Bevacizumab, Bexarotene, Tositumomab, Bicalutamide, Carmustine, Bleomycin, Blinatumomab, Bortezomib, Bosutinib, Brentuximab Vedotin, Busulfan, Cabazitaxel, Cabozantinib—Alemtuzumab), Irinotecan, Capecitabine, CAPDX, Fluorouracil, Carboplatin, carboplatin-taxol, Carfilzomib, Carmustine, Bicalutamide, Lomustine, CEM, Ceritinib, Daunorubicin, Cervarix (Recombinant HPV Bivalent Vaccine), Cetuximab, Chlorambucil, CHOP, Cisplatin, Clofarabine, CMF, Cobimetinib, Cabozantinib, COPDAC, COPP, COPP-ABV, Dactinomycin, Cobimetinib, Crizotinib, CVP, Ifosfamide, Ramucirumab, Cytarabine, Cyclophosphamide, Dabrafenib, Dacarbazine, Decitabine, Dactinomycin, Daratumumab, Dasatinib, Daunorubicin, efibrotide Sodium, Defibrotide, Degarelix, Denileukin Diftitox, Denosumab, DepoCyt (Cytarabine Liposome), Dexamethasone, Dexrazoxane Dinutuximab, Docetaxel, Doxorubicin, Dacarbazine, Rasburicase, Epirubicin, Elotuzumab, Oxaliplatin, Eltrombopag Olamine, Aprepitant, Empliciti (Elotuzumab), Enzalutamide, Epirubicin, EPOCH, Cetuximab, Eribulin, Vismodegib, Erlotinib, Erwinaze (Asparaginase, *Erwinia chrysanthemi*), Etopophos (Etoposide Phosphate), Etoposide, Etoposide Phosphate, Everolimus, Evista (Raloxifene Hydrochloride), Evomela (Melphalan Hydrochloride), Exemestane, 5-FU, Fareston (Toremifene), Farydak (Panobinostat), Faslodex (Fulvestrant), FEC, Letrozole, Filgrastim, Fludarabine, Flutamide, Methotrexate, Folfiri, Folfiri-Bevacizumab, Folfiri-Cetuximab, Folfirinox, Folfox, Pralatrexate, FU-LV, Fulvestrant, Gardasil (Recombinant HPV Quadrivalent Vaccine), Obinutuzumab, Gefitinib, Gemcitabine, Gemtuzumab Ozogamicin, Afatinib, Imatinib, Carmustine, Glucarpidase, Goserelin Acetate, Eribulin, Trastuzumab, Topotecan, HydroxyureaPalbociclib), Ibritumomab Tiuxetan, Ibrutinib, ICE, Ponatinib, Idarubicin, Idelalisib, Ifex (Ifosfamide), Ifosfamide, IL-2 (Aldesleukin), Imatinib Ibrutinib, Imiquimod, Imlygic, Talimogene Laherparepvec, Axitinib, Interferon Alfa-2b, Recombinant, Interleukin-2, Aldesleukin), Intron A (Recombinant Interferon Alfa-2b), Tositumomab, Ipilimumab, Gefitinib, Irinotecan, Romidepsin, Ixabepilone, Ixazomib, Ruxolitinib, Cabazitaxel, Ado-Trastuzumab Emtansine), Raloxifene, Palifermin, Pembrolizumab, Carfilzomib, Lanreotide, Lapatinib, Lenalidomide Lenvatinib, Letrozole, Leucovorin, Leukeran, Chlorambucil), Leuprolide, Olaparib, Vincristine, Procarbazine, Mechlorethamine, Megestrol, Trametinib, Melphalan, Mercaptopurine, Mesna, Temozolomide, Methotrexate, Mitomycin C, Mitoxantrone, MOPP, Plerixafor, Mechlorethamine, Busulfan, Azacitidine, Gemtuzumab Ozogamicin, Vinorelbine, Necitumumab, Nelarabine, Neosar (Cyclophosphamide), Netupitant and Palonosetron Hydrochloride, Neupogen (Filgrastim), Nexavar (Sorafenib Tosylate), Nilotinib, Ninlaro (Ixazomib Citrate), Nivolumab, Nolvadex (Tamoxifen Citrate), Nplate (Romiplostim), Obinutuzumab, Odomzo (Sonidegib), OEPA, Ofatumumab, Olaparib, Omacetaxine Mepesuccinate, Oncaspar (Pegaspargase), Ondansetron Hydrochloride, Onivyde (Irinotecan Hydrochloride Liposome), Ontak (Denileukin Diftitox), Opdivo (Nivolumab), OPPA, Osimertinib, Oxaliplatin, Paclitaxel, Paclitaxel Albumin-stabilized Nanoparticle Formulation, Palbociclib, Palifermin, Palonosetron Hydrochloride, Palonosetron Hydrochloride and Netupitant, Pamidronate Disodium, Panitumumab, Panobinostat, Paraplat (Carboplatin), Paraplatin (Carboplatin), Pazopanib Hydrochloride, Pegaspargase, Peginterferon Alfa-2b, PEG-Intron (Peginterferon Alfa-2b), Pembrolizumab, Pemetrexed Disodium, Perjeta (Pertuzumab), Pertuzumab, Platinol (Cisplatin), Platinol-AQ (Cisplatin), Plerixafor, Pomalidomide, Pomalyst (Pomalidomide), Ponatinib Hydrochloride, Portrazza (Necitumumab), Pralatrexate, Prednisone, Procarbazine Hydrochloride, Proleukin (Aldesleukin), Prolia, Denosumab), Promacta (Eltrombopag Olamine), Provenge (Sipuleucel-T), Purinethol (Mercaptopurine), Purixan (Mercaptopurine), Radium 223 Dichloride, Raloxifene Hydrochloride, Ramucirumab, Rasburicase, R-CHOP, R-CVP, Recombinant Human Papillomavirus (HPV) Bivalent Vaccine, Recombinant Human Papillomavirus (HPV) Nonavalent Vaccine, Recombinant Human Papillomavirus (HPV) Quadrivalent Vaccine, Recombinant Interferon Alfa-2b, Regorafenib, R-EPOCH, Revlimid (Lenalidomide), Rheumatrex (Methotrexate), Rituxan, ituximab), Rituximab, Rolapitant Hydrochloride, Romidepsin, Romiplostim, Rubidomycin, Daunorubicin Hydrochloride), Ruxolitinib Phosphate, Sclerosol Intrapleural Aerosol (Talc), Siltuximab, Sipuleucel-T, Somatuline Depot (Lanreotide Acetate), Sonidegib, Sorafenib Tosylate, Sprycel (Dasatinib), STANFORD V, Sterile Talc Powder (Talc), Steritalc (Talc), Stivarga (Regorafenib), Sunitinib Malate, Sutent (Sunitinib Malate), Sylatron (Peginterferon Alfa-2b), Sylvant (Siltuximab), Synovir (Thalidomide), Synribo (Omacetaxine Mepesuccinate), Tabloid (Thioguanine), TAC, Tafinlar (Dabrafenib), Tagrisso (Osimertinib), Talimogene Laherparepvec, Tamoxifen Citrate, Tarabine PFS (Cytarabine), Tarceva (Erlotinib Hydrochloride), Targretin, Bexarotene), Tasigna (Nilotinib), Taxol (Paclitaxel), Taxotere (Docetaxel), Tecentriq, Atezolizumab), Temodar (Temozolomide), Temozolomide, Temsirolimus, Thalidomide, Thalomid (Thalidomide), Thioguanine, Thiotepa, Tolak (Fluorouracil—Topical), Topotecan Hydrochloride, Toremifene, Torisel (Temsirolimus), Tositumomab and Iodine I 131 Tositumomab, Totect (Dexrazoxane Hydrochloride), Trabectedin, Trametinib, Trastuzumab, Treanda, Bendamustine Hydrochloride), Trifluridine and Tipiracil Hydrochloride, Trisenox (Arsenic Trioxide), Tykerb (Lapatinib Ditosylate), Unituxin (Dinutuximab), Uridine Triacetate, Vandetanib, VAMP, Varubi (Rolapitant Hydrochloride), Vectibix (Panitumumab), Velban (Vinblastine Sulfate), Velcade (Bortezomib), Velsar (Vinblastine Sulfate), Vemurafenib, Venclexta (Venetoclax), Venetoclax, Viadur (Leuprolide Acetate), Vidaza (Azacitidine), Vinblastine Sulfate, Vincasar PFS (Vincristine Sulfate), Vincristine Sulfate, Vincristine Sulfate Liposome, Vinorelbine Tartrate, Vismodegib, Vistogard (Uridine Triacetate), Voraxaze, Glucarpidase), Vorinostat, Votrient (Pazopanib Hydrochloride), Wellcovorin (Leucovorin Calcium), Xalkori (Crizotinib), Xeloda (Capecitabine), XELIRI, XELOX, Xgeva (Denosumab), Xofigo (Radium 223 Dichloride), Xtandi (Enzalutamide), Yervoy (Ipilimumab), Yondelis (Trabectedin), Zaltrap (Ziv-Aflibercept), Zarxio (Filgrastim), Zelboraf (Vemurafenib), Zevalin (Ibritumomab Tiuxetan), Zinecard (Dexrazoxane Hydrochloride), Ziv-Aflibercept, Zofran (Ondansetron Hydrochloride), Zoladex (Goserelin Acetate), Zoledronic Acid, Zolinza (Vorinostat), Zometa (Zoledronic Acid), Zydelig (Idelalisib), Zykadia (Ceritinib), Zytiga (Abiraterone Acetate), and combinations thereof.

The liposomes can contain a mixture of conventional lipids (e.g., the primary lipid) and lipids modified to anchor the polymer-boronic ester shell. Conventional lipids for liposomes are well known, and include phosphatidic acid ("PA"), phosphatidylcholine ("PC"), phosphatidylglycerol ("PG"), phophatidylethanolamine phophatidylinositol ("PI"), and phosphatidylserine ("PS"), sphingomyelin (including brain sphingomyelin), lecithin, lysolecithin, lysophosphatidylethanolamine, cerebrosides, diarachidoylphosphatidylcholine ("DAPC"), didecanoyl-L-alpha-phosphatidylcholine ("DDPC"), dielaidoylphosphatidylcholine ("DEPC"), dilauroylphosphatidylcholine ("DLPC"), dilinoleoylphosphatidylcholine, dimyristoylphosphatidylcholine ("DMPC"), dioleoylphosphatidylcholine ("DOPC"), dipalmitoylphosphatidylcholine ("DPPC"), distearoylphosphatidylcholine ("DSPC"), 1-palmitoyl-2-oleoyl-phosphatidylcholine ("POPC"), diarachidoylphosphatidylglycerol ("DAPG"), didecanoyl-L-alpha-phosphatidylglycerol ("DDPG"), dielaidoylphosphatidylglycerol ("DEPG"), dilauroylphosphatidylglycerol ("DLPG"), dilinoleoylphosphatidylglycerol, dimyristoylphosphatidylglycerol ("DMPG"), dioleoylphosphatidylglycerol ("DOPG"), dipalmitoylphosphatidylglycerol ("DPPG"), distearoylphosphatidylglycerol ("DSPG"), 1-palmitoyl-2-oleoyl-phosphatidylglycerol ("POPG"), diarachidoylphosphatidylethanolamine ("DAPE"), didecanoyl-L-alpha-phosphatidylethanolamine ("DDPE"), dielaidoylphosphatidylethanolamine ("DEPE"), dilauroylphosphatidylethanolamine ("DLPE"), dilinoleoylphosphatidylethanolamine, dimyristoylphosphatidylethanolamine ("DMPE"), dioleoylphosphatidylethanolamine ("DOPE"), dipalmitoylphosphatidylethanolamine ("DPPE"), distearoylphosphatidylethanolamine ("DSPE"), 1-palmitoyl-2-oleoyl-phosphatidylethanolamine ("POPE"), diarachidoylphosphatidylinositol ("DAPI"), didecanoyl-L-alpha-phosphatidylinositol ("DDPI"), dielaidoylphosphatidylinositol ("DEPI"), dilauroylphosphatidylinositol ("DLPI"), dilinoleoylphosphatidylinositol, dimnyristoylphosphatidylinositol ("DMPI") dioleoylphosphatidylinositol ("DOPI"), dipalmitoylphosphatidylinositol ("DPPI"), distearoylphosphatidylinositol ("DSPI"), 1-palmitoyl-2-olcoyl-phosphatidylinositol ("POPI"), diarachidoylphosphatidylserine ("DAPS"), didecanoyl-L-alpha-phosphatidylserine ("DDPS"), dielaidoylphosphatidylserine ("DEPS"), dilauroylphosphatidylserine ("DLPS"), dilinoleoylphosphatidylserine, dimyristoylphosphatidylserine ("DMPS"), dioleoylphosphatidylserine ("DOPS"), dipalmitoylphosphatidylserine ("DPPS"), distearoylphosphatidylserine ("DSP"), 1-palmitoyl-2-olcoyl-phosphatidylserine ("POPS"), diarachidoyl sphingomyelin, didecanoyl sphingomyelin, dielaidoyl sphingomyelin, dilauroyl sphingomyelin, dilinoleoyl sphingomyelin, dimyristoyl sphingomyelin, sphingomyelin, dioleoyl sphingomyelin, dipalmitoyl sphingomyelin, distearoyl sphingomyelin, 1-palmitoyl-2-oleoyl-sphingomyelin, and mixtures thereof.

In some cases the primary lipid may include a mixture of different lipid compounds. In some cases the primary lipid can include a choline lipid component (i.e., one or more lipid compounds include the choline residue) and an ethanolamine lipid component (i.e., one or more lipid compounds including an ethanolamine group, which may be functionalized at the amine position). The weight ratio of the (a) choline lipid component and (b) ethanolamine lipid component can be from 99:1 to 1:99, from 25:1 to 1:25, from 10:1 to 1:10, from 5:1 to 1:5, from 2:1 to 1:2, from 1:1 to 1:100, from 1:1 to 1:50, from 1:1 to 1:25, from 1:1 to 1:10, from 1:1 to 1:5, from 1:1 to 1:2, from 100:1 to 1:1, from 50:1 to 1:1, from 25:1 to 1:1, from 10:1 to 1:1, from 5:1 to 1:1, or from 2:1 to 1:1.

The liposomes may also include cholesterol and/or cholesterol derivatives (i.e., cholesterol that has been functionalized at the hydroxyl position). In other embodiments, no cholesterol and/or cholesterol derivatives are present in the liposome. Exemplary cholesterol derivatives include PEGylated cholesterols, neutral esters, cationic esters, and anionic esters. Cationic esters may be obtained from esterification with amine-containing carboxylic acids, for instance lysine, arginine, 3-dimethylamino propionic acid, or 3-aminopropionic acid. Anionic esters may be obtained from esterification with sulfonic or carboxylic acid containing carboxylic acids, for instance glutamic acid, aspartic acid, succinic acid, or citric acid. When present, the cholesterol and/or cholesterol derivatives may constitute from 0.1-20%, from 0.5-20%, from 0.5-15%, from 0.5-10%, from 1-10%, from 2-10%, from 2.5-10%, from 2.5-7.5%, of from 2.5-5% by weight of the liposome. In preferred embodiments, the cholesterol and/or cholesterol derivative is present in an amount from 2-6% by weight, relative to the total weight of the liposome. As used herein with reference to cholesterol and other liposomal components, the total weight of the liposome refers to the weight prior to encapsulation by the polymer. Unless specified to the contrary, the weight ratio of the component in the liposome is equivalent to the weight ratio of the component in the mixtures used to make the liposome.

Lipids modified to anchor the polymer boronate shell include those having di-hydroxyl (diol) functional groups such as 1,2 diols and 1,3 diols. Such a modified lipid can be designated a "polymer anchor." The term polymer anchor can refer to either the free diol or boronic ester conjugate. Polymer anchors are generally represented by the following formula:

Lipid-Linker-Diol.

In some embodiments, the polymer anchor can have either of the following formulae:

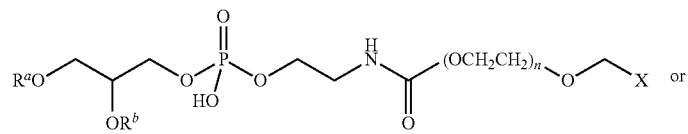

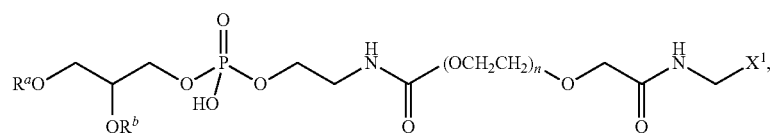

wherein $R^a$ and $R^b$ are independently selected from $C_{6-32}$alkyl-C(O)—, n is an integer from 5-1,000, and X and $X^1$ are diol bearing group. In certain embodiments, n is from 3-1,000, 5-1,000, 8-1,000, 10-1,000, 15-1,000, 20-1,000, 25-1,000, 30-1,000, 35-1,000, 40-1,000, 45-1,000, 50-1,000, 60-1,000, 70-1,000, 80-1,000, 90-1,000, 100-1,000, 125-1,000, 150-1,000, 175-1,000, 200-1,000, 300-1,000, 400-1,000, or 500-1,000. In certain embodiments, $R^a$ and $R^b$ are independently selected from $C_{6-18}$alkyl-C(O)— or $C_{6-32}$alkenyl-C(O). Any of the aforementioned ethanolamine lipid compounds may be used to obtain anchor lipids.

Preferred X and $X^1$ groups include catechols having the formula:

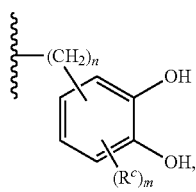

wherein n is an integer from 0-10, preferably 1-6, more preferably 1-4, and even more preferably 1-2, m is an integer from 0-3, and $R^c$ is independently selected from $R^{c1}$, $OR^{c1}$, $N(R^{c1})_2$, $SiR^{c1}_3$, $SR^{c1}$, $SO_2R^{c1}$, $SO_2N(R^{c1})_2$, $C(O)R^{c1}$; $C(O)OR^{c1}$, $OCOR^{c1}$; $C(O)N(R^{c1})_2$, $OC(O)N(R^{c1})_2$, $N(R^{c1})C(O)N(R^{c1})_2$, F, Cl, Br, I, cyano, and nitro, wherein $R^{c1}$ is in each case independently selected from hydrogen, $C_{1-8}$alkyl, $C_{2-8}$alkenyl, $C_{2-8}$alkynyl, aryl, $C_{1-8}$heteroaryl, $C_{3-8}$cycloalkyl, or $C_{1-8}$ heterocyclyl; and wherein any two or more $R^c$ groups may together form a ring.

In certain embodiments, the polymer anchor/boronic ester complex may be represented by the formula:

wherein $R^a$ and $R^b$ are independently selected from $C_{6-32}$alkyl-C(O)—, n is from 3-1,000, 5-1,000, 8-1,000, 10-1,000, 15-1,000, 20-1,000, 25-1,000, 30-1,000, 35-1,000, 40-1,000, 45-1,000, 50-1,000, 60-1,000, 70-1,000, 80-1,000, 90-1,000, 100-1,000, 125-1,000, 150-1,000, 175-1,000, 200-1,000, 300-1,000, 400-1,000, or 500-1,000; and Z and $Z^1$ are:

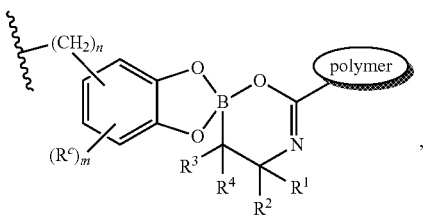

wherein $R^1$, $R^2$, $R^3$, and $R^4$ are independently selected from hydrogen, $C_{1-8}$alkyl, $C_{2-8}$alkenyl, $C_{2-8}$alkynyl, aryl, heteroaryl, $C_{3-8}$cycloalkyl, and $C_{1-8}$heteroaryl, which may be substituted or unsubstituted, and wherein any two or more of $R^1$, $R^2$, $R^3$, and $R^4$ may together form a ring; n is an integer from 0-10, m is an integer from 0-3, and W is independently selected from $R^{c1}$, $OR^{c1}$, $N(R^{c1})_2$, $SiR^{c1}_3$, $SR^{c1}$, $SO_2R^{c1}$, $SO_2N(R^{c1})_2$, $C(O)R^{c1}$; $C(O)OR^{c1}$, $OCOR^{c1}$; $C(O)N(R^{c1})_2$, $OC(O)N(R^{c1})_2$, $N(R^{c1})C(O)N(R^{c1})_2$, F, Cl, Br, I, cyano, and nitro, wherein $R^{c1}$ is in each case independently selected from hydrogen, $C_{1-8}$ alkyl, $C_{2-8}$ alkenyl, $C_{2-8}$ alkynyl, aryl, $C_{1-8}$ heteroaryl, $C_{3-8}$cycloalkyl, or $C_{1-8}$heterocyclyl; and wherein any two or more $R^c$ groups may together form a ring.

In some embodiments, the polymer anchor can be represented by the following formula:

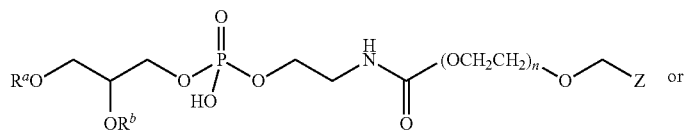

or

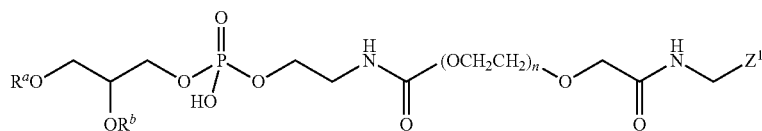

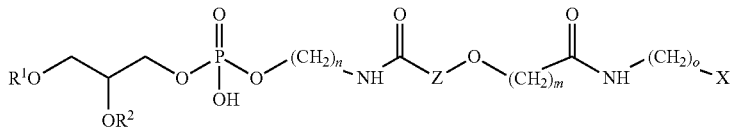

or a pharmaceutically acceptable salt thereof, for instance, sodium, wherein $R^1$ and $R^2$ are selected from acyl, n is selected from 2-10, m is selected from 0-10, o is selected from 0-10, Z is PEG, and X is a 1,2 diol or 1,3 diol containing moiety. In certain embodiments, Z includes a catechol containing group. Suitable acyl groups include $C_{6-24}$ acyl, $C_{6-18}$ acyl, $C_{6-14}$ acyl; the acyl groups may contain one or more olefinic bonds. In certain cases, $R^1$ and $R^2$ can be independently selected from oleoyl, stearoyl, palmitoyl and myristoyl. PEG chains having at least 3, 5, 8, 10, 15, 20, 25, 30, 35, 40, 45, 50, 60, 70, 80, 90, 100, 125, 150, 175 or 200 monomer units can be used in the linker portion, for instance, the polymer anchor can include from 3-1,000, 5-1,000, 8-1,000, 10-1,000, 15-1,000, 20-1,000, 25-1,000, 30-1,000, 35-1,000, 40-1,000, 45-1,000, 50-1,000, 60-1,000, 70-1,000, 80-1,000, 90-1,000, 100-1,000, 125-1,000, 150-1,000, 175-1,000, 200-1,000, 300-1,000, 400-1,000, or 500-1,000 monomer units. In certain embodiments, the polymer anchor can have the following formula:

factor can be tethered to the surface of the liposome using a factor anchor, generally represented by the following formula:

Lipid-Linker-Targeting Factor

Lipids can be modified with targeting factors using conventional bioconjugation chemistries. For example, a lipid may be modified with a functional group that reacts to form a covalent bond with the targeting factor. Non-limiting functional groups include succinimidyl esters, succinimidyl carbonates, succinimidyl carbamates, pentafluorophenyl esters, thioazolidine-2-thiones, anhydrides, aldehydes, Michael acceptors such as vinyl sulfone, maleimide; alkynes (for reaction with azide modified factors), or azides (for reaction with alkyne-modified factors). When present, the factor anchor can be present in the liposome in an amount from 0.05-10%, from 0.1-10%, from 0.1-7.5%, from 0.1-5%, from 0.1-4%, from 0.1-3%, from 0.1-2%, from 0.1-1%, from 0.5-10%, from 0.5-7.5%, from 0.5-5%, from 0.5-4%, from 0.5-3%, from 0.5-2%, or from 0.5-1% by weight, relative to the total weight of the liposome. In certain preferred embodiments, the factor anchor is present in an

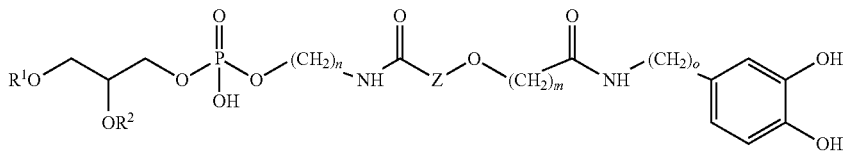

or a pharmaceutically acceptable salt thereof, wherein $R^1$, $R^2$, n, m, o and Z have the meanings given above. In some cases, $R^1$ and $R^2$ can each be stearoyl, n can be 2, Z can be PEG, m can be 1, and o can be 2.

The polymer anchor can be present in the liposome in an amount from 0.05-10%, from 0.1-10%, from 0.1-7.5%, from 0.1-5%, from 0.1-4%, from 0.1-3%, from 0.1-2%, from 0.1-1%, from 0.5-10%, from 0.5-7.5%, from 0.5-5%, from 0.5-4%, from 0.5-3%, from 0.5-2%, or from 0.5-1% by weight, relative to the total weight of the liposome. In certain preferred embodiments, the polymer anchor is present in an amount from 0.5-2%, by weight relative to the total weight of the liposome.

In certain embodiments, the drug delivery system can further include one or more targeting factors to facilitate absorption of the therapeutic agent. For instance, the composition can include human IgG Fc fragments. Other suitable targeting factors include transferrin (Tf) and anti-intercellular adhesion molecule-1 (ICAM-1). The targeting amount from 0.5-2%, by weight relative to the total weight of the liposome. The targeting factor itself is not included in the calculation of the relative weight of the factor anchor.

In some embodiments, the polymer anchor and factor anchor each include a hydrophilic moiety, such as polyethylene glycol. In some embodiments, the PEG moiety in the factor anchor is shorter than the PEG moiety in the polymer anchor, in order that the targeting factor is encapsulated well by the polymer. For instance, the number of ethylene oxide units in the factor anchor can be no more than 95%, no more than 90%, no more than 85%, no more than 80%, no more than 75%, no more than 70%, no more than 65%, no more than 60%, no more than 55%, no more than 50%, no more than 45%, no more than 40%, no more than 35%, no more than 30%, no more than 25%, no more than 20%, no more than 15%, no more than 10%, or no more than 5% the number of ethylene oxide units in the polymer anchor.

The factor can be installed via reaction of the targeting factor with a compound of the formula:

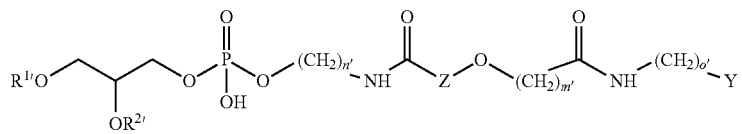

or a pharmaceutically acceptable salt thereof, wherein $R^{1'}$ and $R^{2'}$ are selected from acyl, n' is selected from 2-10, m' is selected from 0-10, o' is selected from 0-10, Z' is PEG, and Y is moiety capable of reacting with the targeting moiety to form a covalent bond. In some embodiments, Y can be a succinimidyl ester, succinimidyl carbonate, succinimidyl carbamate, pentafluorophenyl ester, a thioazolidine-2-thione, an anhydride, an aldehyde, a Michael acceptor such as vinyl sulfone, maleimide, alkyne (for reaction with azide modified factors), or an azide (for reaction with alkyne-modified factors).

Suitable acyl groups include $C_{8-24}$ acyl, $C_{6-18}$ acyl, $C_{6-14}$ acyl; the acyl groups may contain one or more olefinic bonds. In certain cases, R" and $R^{2'}$ can be independently selected from oleoyl, stearoyl, palmitoyl and myristoyl. PEG chains having at least 3, 5, 8, 10, 15, 20, 25, 30, 35, 40, 45, 50, 60, 70, 80, 90, 100, 125, 150, 175 or 200 monomer units can be used in the linker portion, for instance, the linker can include from 5-200, 10-150, 20-150, 20-100, or 25-75 monomer units. In certain embodiments, the targeting factor can be reacted with a compound having the following formula:

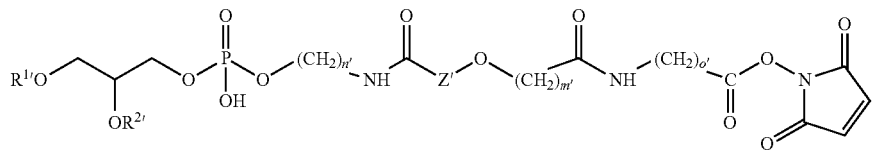

or a pharmaceutically acceptable salt thereof, wherein $R^{1'}$, $R^{2'}$, n', m', o' and Z' have the meanings given above. For instance, R" and $R^{2'}$ can each be stearoyl, n' can be 2, Z' can be PEG, m' can be 1, and o' can be 2. In some cases, the targeting factor can be in its native state when conjugated to the polymer anchor. In other cases, the reactivity of the targeting factor can be increased, for instance by reacting the factor with a thiolating agent like Traut's reagent. In other cases, reductants like Cleland's reagent can be used. Generally it is preferred to conjugate the factor and factor anchor after forming the liposome, but in some cases the conjugation can take place prior to liposome formation.

Liposomes can be formed by conventional methods. In a preferred method, the lipids are dissolved or dispersed in a volatile solvent, and then evaporated to form a film. An aqueous solution containing the therapeutic agent can be added to the film followed by mechanical dispersion, for instance using sonication. The mixture can be extruded through one or more filters to yield the liposomes. If not already attached, a targeting factor can be conjugated to the liposome using conventional maleimide-thiol chemistry. The liposomes can be combined with the polymer-boronic ester complex and stirred at room temperature to give the polymer encapsulated liposomes.

Apparatuses for determining the average particle diameter and the size distribution are commercially available. These typically use the techniques of dynamic light scattering and/or single-particle optical sensing e.g. the Accusizer™ and Nicomp™ series of instruments available from Particle Sizing Systems (Santa Barbara, USA), or the Zetasizer™ instruments from Malvern Instruments (UK), or the Particle Size Distribution Analyzer instruments from Horiba (Kyoto, Japan). Dynamic light scattering is the preferred method by which encapsulated liposome diameters are determined. For a population of encapsulated liposomes, the preferred method for defining the average liposome diameter in a composition of the invention is a Z-average i.e. the intensity-weighted mean hydrodynamic size of the ensemble collection of liposomes measured by dynamic light scattering (DLS). The Z-average is derived from cumulants analysis of the measured correlation curve, wherein a single particle size (liposome diameter) is assumed and a single exponential fit is applied to the autocorrelation function. The cumulants analysis algorithm does not yield a distribution but, in addition to an intensity-weighted Z-average, gives a polydispersity index.

The encapsulated liposomes disclosed herein can be prepared in a variety of different particle sizes. Preferred sizes include from 1-10,000 nm, from 1-5,000 nm, from 1-2,500 nm, from 1-1,000 nm, from 1-750 nm, from 1-500 nm, from 1-250 nm, from 5-250 nm, from 25-250 nm, from 50-250 nm, or from 75-150 nm, as measured by the dynamic light scattering methods. In other cases, the encapsulated liposome can have a particle size, as measured by the dynamic light scattering methods, from 100-10,000 nm, from 250-10,000 nm, from 500-10,000 nm, from 100-5,000 nm, from 250-5,000 nm, from 500-5,000 nm, from 100-2,500 nm, from 250-2,500 nm, from 500-2,500 nm, from 100-1,000 nm, from 250-1,000 nm, or from 500-1.00 nm.

Generally, the targeting protein will be located at the surface of the liposome, and is also encapsulated by the hyaluronic acid shell. In some embodiments, neonatal Fc receptor (FcRn)-targeted liposome core is loaded with insulin (FIG. 1A). FcRn is expressed in the apical region of epithelial cells in the small intestine, which can bind IgG via the Fc portion, thereby facilitating protein transport across the intestinal epithelium into the circulation. This specific binding functions in a pH-dependent manner, showing high affinity in the apical side (pH 5.5-6.5) of the duodenal enterocytes but not in the basolateral side (pH 7.4).

The aminoboronic acid conjugated HA shell, which coats the liposome core through the boronate ester formation between aminoboronic acid and diol groups on the liposome surface, can prevent the leakage and digestion of the therapeutic agent in the gastrointestinal tract, and additionally serves as a glucose-responsive moiety for on-demand absorption. In elevated postprandial glucose concentrations in the intestine that occurring during meal digestion, the HA shell detaches due to the competitive binding of glucose with aminoboronic acid (FIG. 1B), exposing the targeting factors groups which promote the intestinal absorption of therapeutic-loaded liposome core to ultimately release the agent in the bloodstream.

Preparation and Characterization of Glucose-Responsive Insulin-Loaded Liposomes.

Figure 2:
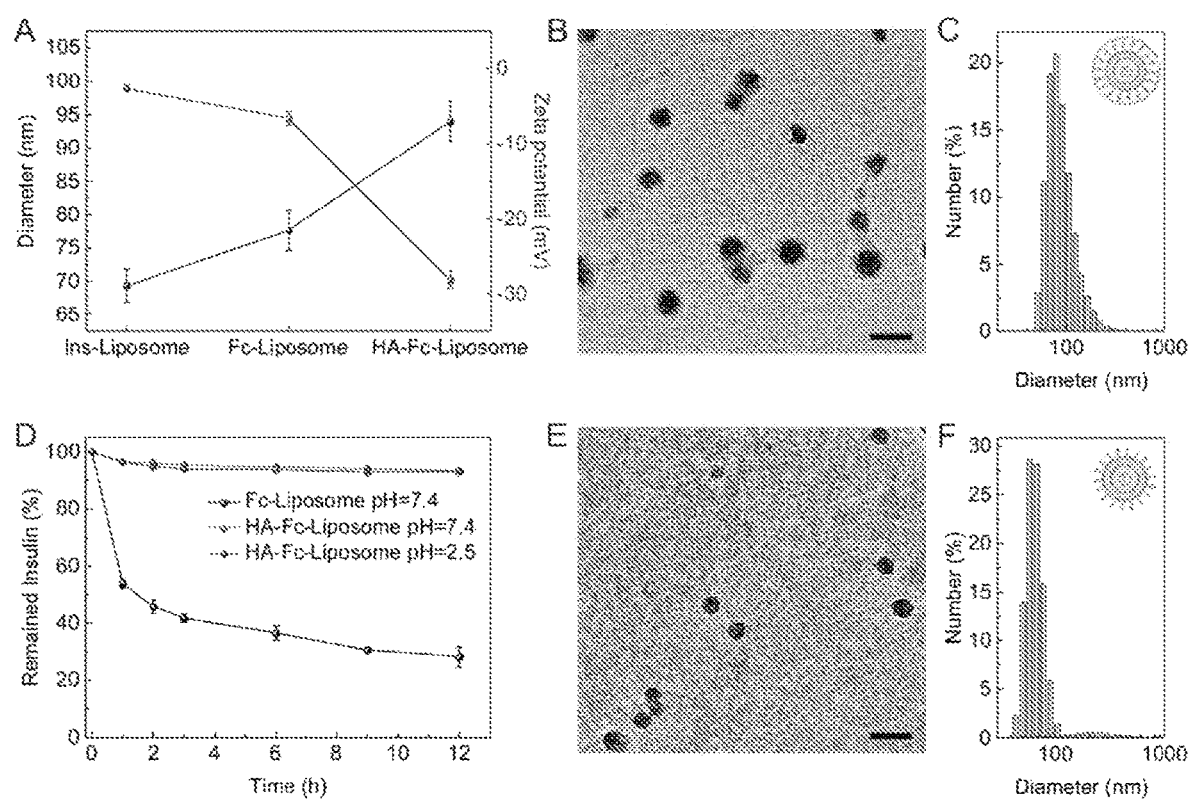
FIG. 2 includes a characterization of glucose-responsive HA-Fc-Liposomes. (A) The particle size and zeta potential of Ins-Liposome, Fc-Liposome, and HA-Fc-Liposome. (B) TEM image of HA-Fc-Liposomes. Scale bar: 100 nm. (C) The hydrodynamic size distribution of HA-Fc-Liposome measured by dynamic light scattering (DLS). (D) In vitro release of insulin from Fc-Liposome and HA-Fc-Liposome under pH 7.4 or 2.5. Error bars indicate SD (n=3). (E) TEM image and (F) the size distribution of HA-Fc-Liposomes after 2 h incubation with glucose (10 mM). Scale bar is 100 nm.
Figure 5:
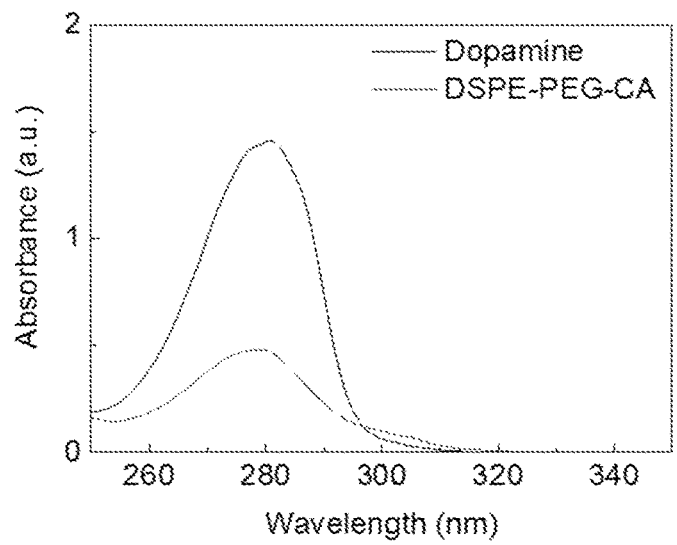
FIG. 5 depicts UV-Vis spectra of Dopamine (1 mg/mL), and DSPE-PEG-CA (10 mg/mL) in water.
Figure 6:
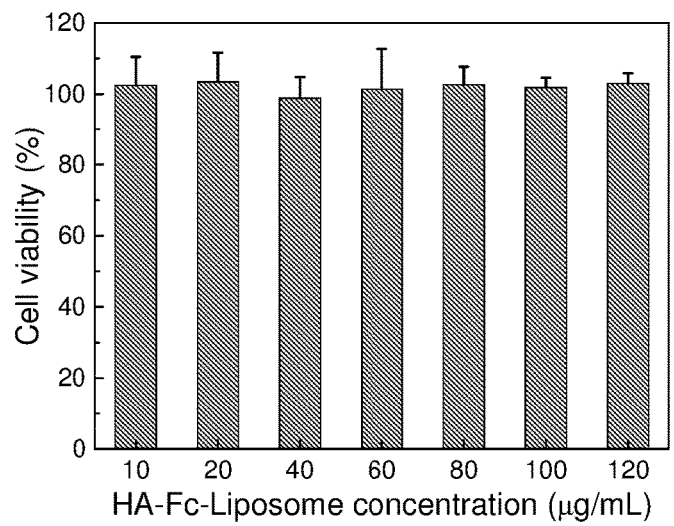
FIG. 6 depicts Cytotoxicity study of empty HA-Fc-Liposomes after 24 h of incubation with Caco-2 cells. Error bars indicate SD (n=6).

The insulin-loaded liposomes (Ins-Liposomes) were first prepared using the lipid film hydration method. In order to prepare liposomes with catechol (CA) groups on the surface, dopamine was first conjugated to the carboxyl groups of DSPE-PEG-CM (1,2-distearoyl-sn-glycero-3-phosphoethanolamine-N-[carboxy(polyethylene glycol)]) to achieve DSPE-PEG-CA using carbodiimide chemistry. The successful conjugation was verified through UV-Vis spectra (FIG. 5). The obtained Ins-Liposomes had an average diameter of approximately 69 nm and a zeta potential of −2.6 mV (FIG. 2A). The encapsulation efficiency (EE) and loading capacity (LC) of insulin in Ins-Liposomes were determined to be 20.7% and 17.1%, respectively. Polyclonal IgG Fc fragments was covalently conjugated to PEG chain on the surface of Ins-Liposomes using maleimide-thiol chemistry. 2-Iminothiolane was used to modify the Fc with thiol groups. After the conjugation, the hydrodynamic diameter of the Fc-Liposomes increased to 77 nm, and the surface charge showed a minor change to −6.6 mV. The HA shell was further coated on the Fc-Liposome via the combination between PBA and catechol groups. The resulting liposomes with HA shell (HA-Fc-Liposome) had an increasing size of around 94 nm (FIG. 2C). The HA-Fc-Liposome showed a significant change in zeta potential from −6.6 mV to −28.1 mV confirmed the successful the formation of HA shell. The transmission electron microscopy (TEM) image clearly revealed the core-shell structure of HA-Fc-Liposomes (FIG. 2B). The blank HA-Fc-Liposome showed insignificant cytotoxicity towards human intestinal epithelial colorectal adenocarcinoma (Caco-2) cells (FIG. 6).

The HA shell was expected to not only act as a glucose-responsive moiety, but also prevent the leakage and digestion of insulin in the upper gastrointestinal tract. A quick release of insulin from Fc-Liposomes was observed under pH 7.4 at 37° C. As shown in FIG. 2D, around 50% of insulin was released within 2 h. However, there was negligible leakage of insulin from HA-Fc-Liposomes under the same conditions, which can be attributed to the HA coating. Importantly, insulin levels were nearly completely maintained in the HA-Fc-Liposome under pH 2.5, demonstrating high stability of this insulin carrier in the acidic conditions of the stomach.

EXAMPLES

The following examples are for the purpose of illustration of the invention only and are not intended to limit the scope of the present invention in any manner whatsoever. The skilled person will be able to prepare other compositions as described herein by modification of the processes discloses below.

Glucose-Responsive Detachment of HA Shell.

Figure 3:
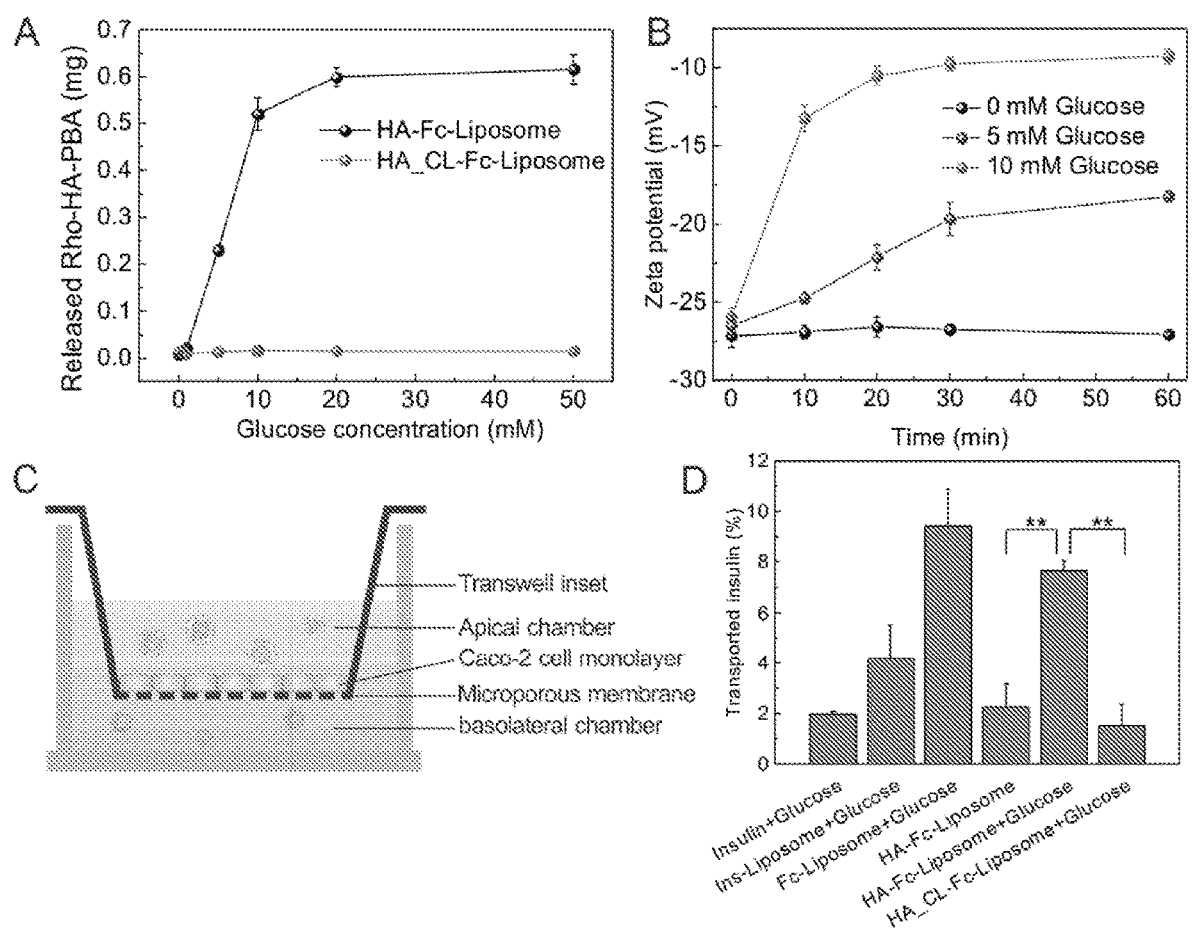
FIG. 3 depicts in vitro glucose-triggered HA shell detachment from HA-Fc-Liposome and transepithelial transport. (A) In vitro detachment of Rho-HA-PBA from HA-Fc-Liposome or HA_CL-Fc-Liposome under different glucose concentrations under pH 6.0. (B) The zeta-potential change of HA-Fc-Liposome in 0, 5, and 10 mM glucose solution over time. (C) Schematic of In vitro transepithelial transport study using Caco-2 cell monolayer permeability assay. (D) In vitro transepithelial transport of different insulin-loaded liposome formulations with or without 10 mM glucose. Error bars indicate SD (n=3). **P<0.01 (two-tailed Student's t-test).
Figure 7:
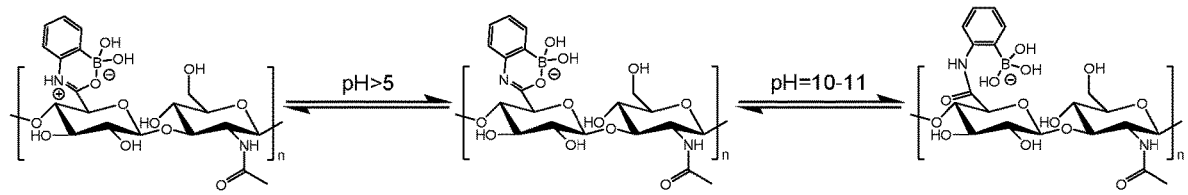
FIG. 7 depicts the equilibrium of HA-PBA in water: intramolecular B—O bond formation leads to the tetrahedral geometry of the boron atom that promotes boronate ester formation.
Figure 8:
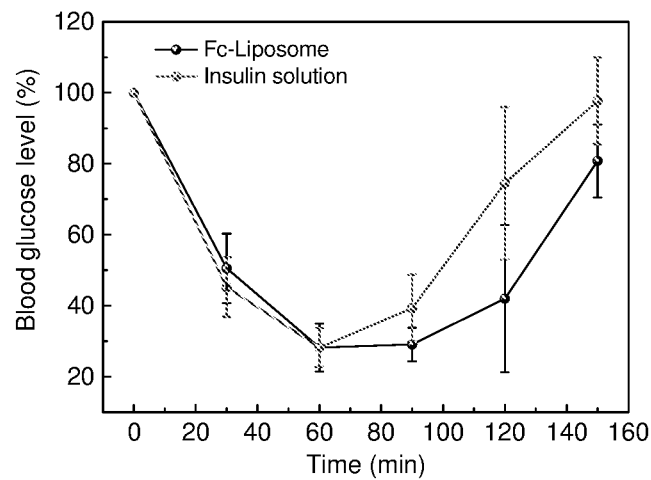
FIG. 8 depicts blood glucose changes of diabetic mice after i.v. injection of insulin solution or insulin-loaded Fc-Liposome (insulin dose: 5 U/kg). Error bars indicate SD (n=5).

The PBA modified HA polymer (HA-PBA) was used to coat the surface of Fc-Liposomes based on the complexation between catechol and PBA through formation of boronate esters (25). Due to the intramolecular coordination that can stabilize boronate ester formation at mildly acidic condition (FIG. 7), the boronate ester formation was dynamically stable in intestine fluid (pH 5.5-8.0). However, this kind of boronate ester can be destroyed in the presence of glucose due to competitive binding of glucose with PBA, thereby rendering the HA shell glucose-responsive. To verify the detachment of the HA shell under high glucose concentrations, the HA-Fc-Liposomes containing rhodamine-labelled HA-PBA (Rho-HA-PBA) were incubated in PBS buffer with increasing glucose concentrations. For comparison purposes, we also prepared the liposomes coated with acrylate modified Rho-HA-PBA shell, which was further crosslinked with N,N'-methylenebisacrylamide under UV irradiation. The liposome coated with crosslinked HA shell (HA_CL-Fc-Liposome) cannot respond to glucose and thus serves as a control. As shown in FIG. 3A, a marked release of Rho-HA-PBA was observed after incubation with 5, 10, 20, and 50 mM glucose for 30 min. The morphological change in TEM image and the decrease in size further verified that incubation with 10 mM glucose was sufficient for complete detachment of the HA shell (FIGS. 2E and F). However, insignificant release was observed from HA_CL-Fc-Liposomes in all glucose conditions. Zeta potential results further validated the detachment of the HA shell and the subsequent exposure of Fc groups. As shown in FIG. 3B, the surface charge increased from −25.9 mV to −9.7 mV after 30 min incubation with 10 mM glucose, indicating the quick release of Fc-Liposome core. To determine the effect of the released insulin on blood glucose, insulin-loaded Fc-Liposomes were collected and intravenously injected into streptozotocin (STZ)-induced adult type 1 diabetic C57BL/6J mice (insulin dose: 5 U/kg). Fc-Liposomes were able to generate a hypoglycemic response (FIG. 8) comparable to that of injection of native insulin, confirming the successful release of bioactive insulin.

Figure 9:
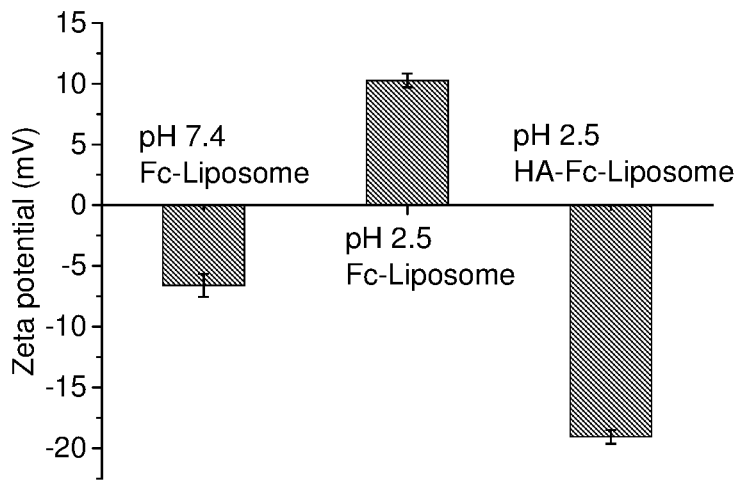
FIG. 9 depicts zeta potential of Fc-Liposome and HA-Fc-Liposome under pH 2.5 and 7.4. Error bars indicate SD (n=3).

Since the formation of boronate ester is inhibited in a strong acidic condition in the stomach (pH 1.2-3.0), the HA-PBA could not form the complexation with the catechol groups on the surface of the Fc-Liposome core. However, due to the protonation of surface groups on the Fc-Liposomes in acidic condition, the negative surface charge of Fc-Liposomes was converted to a positive charge under pH 2.5 (FIG. 9), which kept the intact HA shell by electrostatic interaction. Taken together, the HA shell was shown to prevent the leakage and digestion of insulin in the stomach.

In Vitro Transepithelial Transport.

In vitro transepithelial transport efficiency of insulin-loaded liposomes was next evaluated using the human intestinal epithelial colorectal adenocarcinoma (Caco-2) cell monolayer permeability assay. As shown in FIG. 3C, FITC-labelled insulin-loaded liposomes were added to the apical chamber over the cell monolayer and incubated with or without glucose at 37° C. for 2 h. The transepithelial transport efficiency was determined by measuring the fluorescence intensity of FITC-labelled insulin in the basolateral chamber. Since FcRn is highly expressed on the surface of Caco-2 cells, higher transepithelial permeability of Fc-Liposomes was observed due to FcRn-mediated transcytosis compared to Ins-liposomes (FIG. 3D). Unlike liposomes with crosslinked HA shell (HA_CL-Fc-Liposomes), the co-incubation with glucose also increased the transport of HA-Fc-Liposomes, indicating the Fc groups were exposed after glucose-triggered detachment of the HA shell.

In Vivo Intestinal Absorption.

Figure 4:
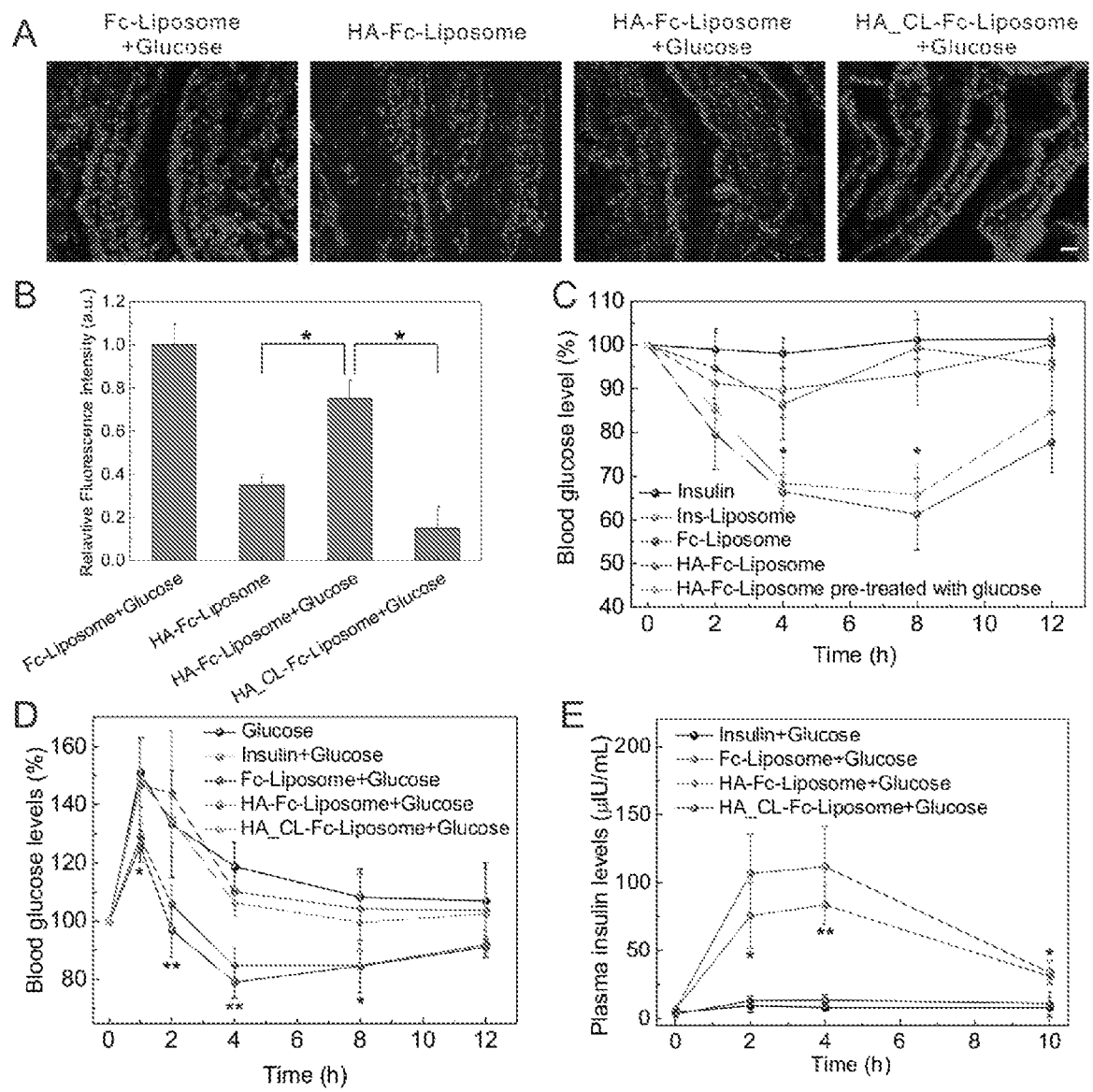
FIG. 4 depicts in vivo studies for type 1 diabetes treatment. (A) Fasted STZ-induced type 1 diabetic mice were orally administered with different formulation: 1) Fc-Liposome+glucose; 2) HA-Fc-Liposome; 3) HA-Fc-Liposome+glucose; 4) HA_CL-Fc-Liposome+glucose. The intestines were collected for sectioning and imaging 2 h after administration. Green fluorescence indicated FITC-labelled insulin, and blue fluorescence indicated Hoechst 33342-stained nuclei. Scale bar: 20 µm. (B) Quantitative analysis of the fluorescence intensities in the in vivo FITC-insulin absorption. All the fluorescence intensities were normalized to the Fc-Liposome+Glucose group. *P<0.05 (two-tailed Student's t-test). (C) Blood glucose levels of fasted diabetic mice after oral administration of insulin solution, Insulin-loaded Liposome, Fc-Liposome, HA-Fc-Liposome, and HA-Fc-Liposome pre-treated with glucose. *P<0.05 for administration with HA-Fc-Liposome pre-treated with glucose (10 mM) compared with HA-Fc-Liposome. (D) Blood glucose levels of fasted mice orally administered with different formulation: 1) Glucose; 2) Insulin solution+glucose; 3) Fc-Liposome+glucose; 4) HA-Fc-Liposome+glucose; 5) HA_CL-Fc-Liposome+glucose. Glucose solution (1 g/kg) was orally administered post 30 min oral intake of insulin formulation (10 U/kg). (E) Plasma human insulin concentrations in diabetic mice after treatment. *P<0.05 and **P<0.01 for administration with HA-Fc-Liposome+glucose compared with HA_CL-Fc-Liposome+glucose. Error bars indicate SD (n=5).

STZ-induced type 1 diabetic mice were divided into four groups and sequentially administered by oral gavage 1) Fc-Liposome+glucose; 2) HA-Fc-Liposome; 3) HA-Fc-Liposome+glucose; 4) HA_CL-Fc-Liposome+glucose. Oral intake of glucose solution (1 g/kg) post 30 min oral intake of liposome was used to simulate the postprandial condition. Duodenum sections were collected and imaged 2 h after administration using fluorescence microscopy. As shown in FIG. 4A, the green fluorescence of FITC-labelled insulin was ubiquitously observed in the villi from the Fc-Liposome+glucose-treated groups yet rarely observed in the mice treated with HA-Fc-Liposome. Moreover, the additional intake of glucose solution led to the obvious distribution of FITC fluorescence in the villi from the mice treated HA-Fc-Liposome+glucose. There was little fluorescence signal found in the section from HA_CL-Fc-Liposome+glucose-treated mice, as expected. Quantitative data further indicated oral administration of HA-Fc-Liposome+glucose resulted in a 5-fold increase in the amount of FITC-labelled insulin in the villi on the basolateral side of the epithelial cells compared to the HA_CL-Fc-Liposome+glucose-treated group (FIG. 4B).

Glucose-Responsive Oral Delivery of Insulin for Type 1 Diabetes Treatment.

The hypoglycemic effect generated by oral administration of insulin-loaded liposomes with or without Fc was assessed on diabetic mice (Insulin dose: 10 U/kg). Oral intake of Fc-Liposomes induced a significant decline in blood glucose levels during the first 12 h after treatment (FIG. 4C). However, the oral treatment with free insulin did not induce a hypoglycemic response, and the treatment of Ins-Liposomes or HA-Fc-Liposomes led to minimal reduction in blood glucose levels. Of note, the oral administration of HA-Fc-Liposomes that had been previously treated with 10 mM glucose also showed a similar effect on glycemic control compared to Fc-Liposomes, indicating the exposed Fc improved the intestinal absorption of the liposomes after the glucose-triggered detachment of HA shell.

Next, we assessed the glucose-responsive intestinal absorption of liposomes by oral administration of glucose solution to simulate the postprandial condition. Glucose solution (1 g/kg) was orally administered to mice 30 min after the oral administration of insulin-loaded formulations of varying concentration. As demonstrated in FIG. 4D, oral administration of glucose solution led to a postprandial hyperglycemia, and the blood glucose levels reduced to the initial level after 8 h of treatment. Pre-treatment of insulin-loaded Fc-Liposomes significantly suppressed the postprandial elevation of blood glucose, where blood glucose levels returned to initial levels after 2 h of oral glucose treatment and remained at such reduced levels for 8 h. Treatment with glucose-responsive HA-Fc-Liposomes similarly exhibited a hypoglycemic effect due to the Fc-mediated intestinal absorption of insulin-loaded liposomes after the detachment of HA shell, triggered by high glucose concentration in the intestine after oral glucose administration. However, a significant lasting postprandial increase of blood glucose was observed in the group administered HA_CL-Fc-Liposome, which further verified the hypoglycemic effect of this insulin delivery system was dependent on the intestinal glucose-triggered detachment of HA shell. Correspondingly, mice treated with HA-Fc-Liposomes presented a consistently higher plasma insulin concentration than those treated with HA_CL-Fc-Liposome (FIG. 4E).

Methods

Materials.

All chemicals were purchased from Sigma-Aldrich unless otherwise specified and were used as received. Sodium hyaluronic acid (molecular weight: 300 kDa) was purchased from Freda Biochem Co., Ltd. (Shandong, China). Human recombinant insulin (Zn salt, 27.5 IU/mg) was purchased from Life Technology. Purified human polyclonal IgG Fc was purchased from Bethyl Laboratories. 1,2-distearoyl-sn-glycero-3-phosphoethanolamine-N-[maleimide(polyethylene glycol)] (DSPE-PEG-MAL) (MW=2000) and 1,2-distearoyl-sn-glycero-3-phosphoethanolamine-N-[carboxy (polyethylene glycol)] (DSPE-PEG-CM) (MW=2000) were purchased from Laysan Bio, Inc.

Synthesis and Characterization of Glucose-Responsive Hyaluronic Acid (HA-PBA), Acrylate Modified HA-PBA, and Rhodamine-Labelled HA-PBA.

Acrylate modified HA and rhodamine-labelled HA were synthesized follow the literature (37, 38). 2-Aminophenylboronic was conjugated to HA in the presence of 1-ethyl-3-(3-dimethylaminopropyl)carbodiimide hydrochloride (EDC) and N-hydroxysuccinimide (NHS). Briefly, 0.5 g of HA (molecular weight: ~300 kDa) was dissolved in water, to which EDC (0.58 g) and NHS (0.35 g) were added and stirred for 15 min at room temperature (RT). Then 2-aminophenylboronic acid hydrochloride (0.17 g) was added to the mixture and react at RT overnight. The reaction solution was thoroughly dialyzed against DI water for 3 days. Then, HA-PBA was obtained by lyophilization and characterized by $^1$H NMR. The degree of modification was calculated to be 14.4% by comparing the ratio of the areas under the proton peaks at 6.91-7.40 ppm to the peak at 1.99 ppm. $^1$H NMR (400 MHz, D$_2$O, δ): 7.40 (s, H, phenyl-H), 7.20 (s, 2H, phenyl-H), 6.91 (s, H, phenyl-H). Acrylate modified HA-PBA and rhodamine-labelled HA-PBA were synthesized in a similar protocol.

Synthesis and Characterization of Catechol-Modified DSPE-PEG-CM (DSPE-PEG-CA).

DSPE-PEG-CM (200 mg), EDC (57.5 mg), and NHS (34.5 mg) were mixed and dissolved in 20 mL DI water and stirred for 30 min at RT. Dopamine hydrochloride (57 mg) was then added to the mixture and stirred for 8 h at RT. The unreacted dopamine was removed by dialysis against DI water for 2 d. The obtained DSPE-PEG-CA was lyophilized and stored at 4° C. until use. The successful conjugation was verified by measuring the UV-Vis absorption of catechol groups using a Nanodrop 2000C spectrometer (Thermo Scientific).

Preparation of Glucose-Responsive Liposomes Loaded with Insulin.

First, the insulin-loaded liposome was prepared by the lipid film hydration method. Briefly, a mixture of egg phosphatidylcholine (EPC), dioleoylphosphatidylethanolamine (DOPE), DSPE-PEG-MAL, DSPE-PEG-CA and cholesterol (weight ratio=9:9:1:1:4) was dissolved in chloroform. The solution was evaporated dry to form the lipid film. The formed lipid film was hydrated with HEPES buffer (5 mM) containing insulin (insulin:lipids, 1:1, w:w), dispersed by a probe-type ultrasonicator, and extruded 3 times through the membrane filters with the pore size of 0.45 and 0.20 μm successively. The non-encapsulated insulin was removed by centrifugation at 21,000 rpm and the resulting Ins-Liposomes were washed 3 time by PBS buffer containing 5 mM EDTA. The encapsulation efficiency (EE) and loading capacity (LC) of insulin in Ins-Liposomes were determined by measuring the amount of non-encapsulated insulin using a Coomassie Plus protein assay.

Fc-Liposomes were obtained by conjugation of Fc to PEG chain on the surface of Ins-Liposomes using maleimide-thiol chemistry. Briefly, 86 μg of purified human polyclonal IgG Fc in PBS containing 5 mM EDTA was reacted with 4.8 μL of Traut's Reagent (0.5 mg/mL) for 1 h. The modified Fc was then added to the Ins-Liposomes and mixed for 1 h at 4° C. The resulting Fc-Liposomes were collected by centrifugation at 21,000 rpm and washed with PBS buffer 3 times.

The obtained Fc-Liposome solution was added to the HA-PBA solution (HA-PBA:lipids, 1:10, w:w) and mixed for 2 h. The HA-Fc-Liposomes were obtained by centrifugation at 21,000 rpm and washed with PBS buffer. The zeta potential and size distribution were measured on the Zetasizer (Nano ZS, Malvern). The transmission electron microscopy (TEM) images of HA-Fc-Liposomes were obtained on a JEOL 2000FX TEM instrument.

The liposomes with non-glucose-responsive HA shell (HA_CL-Fc-Liposomes) were prepared by crosslinking HA shell via UV irradiation. The Fc-Liposomes were added into the acrylate modified HA-PBA solution (HA-PBA:lipids, 1:10, w:w) and stirred for 2 h. A crosslinker N,N-methylenebisacrylamide (MBA) (MBA:HA-PBA, 1:5, w:w) and a photo-initiator Irgacure 2959 (0.1%, w:v) was then added to the mixture. After radical polymerization via UV radiation for 60 s using a BlueWave 75 UV Curing Spot Lamp (DYMAX), HA_CL-Fc-Liposomes were obtained by centrifugation at 21,000 rpm and washed with PBS buffer.

In Vitro Detachment of HA Shell.

To evaluate the glucose-responsive detachment of HA-PBA shell, HA-Fc-Liposomes or HA_CL-Fc-Liposomes containing rhodamine-labelled HA-PBA were incubated under pH 6.0 with different glucose concentrations (1, 5, 10, 20, and 50 mM) at 37° C. for 1 h. The detached Rho-HA-PBA were separated by centrifugation at 21,000 rpm. The fluorescence intensity of free Rho-HA-PBA was determined at 575 nm with an excitation wavelength of 552 nm by a microplate reader (Infinite M200 PRO, Tecan).

In Vitro Insulin Release.

To evaluate the in vitro insulin release profile, FITC-insulin-loaded HA-Fc-Liposomes or Fc-Liposomes were suspended in Tris-HCl buffer (10 mM, pH 7.4) or Tris-HCl buffer (10 mM, pH 2.5). At prearranged time intervals, released insulin was harvested by centrifugation at 21,000 rpm. The fluorescence intensity of free FITC-insulin was determined at 519 nm with the excitation wavelength at 495 nm.

Cell Culture.

Caco-2 cells were obtained from Tissue Culture Facility of UNC Lineberger Comprehensive Cancer Center and cultured in Dulbecco's Modified Eagle's Medium supplemented with 10% (v/v) fetal bovine serum (FBS), penicillin (100 U/mL) and streptomycin (100 μg/mL) in a 37° C. incubator (Thermal Scientific) under 5% $CO_2$ and 90% humidity. The cells were regularly sub-cultured with trypsin-EDTA (0.25%, w/w) and cell density was determined with hemocytometer before each experiment.

In Vitro Cytotoxicity.

The cytotoxicity of the glucose-responsive HA-Fc-Liposomes was evaluated using 3-(4,5)-dimethylthiahiazo(-zyl)-3,5-di-phenytetrazoliumromide (MTT) assay with Caco-2 cells. Prior to the test, the medium in 96-well plate was removed. After washing with PBS, series dilutions of bare HA-Fc-Liposomes were added into wells. After 24 h incubation, thiazolyl blue solution (5 mg/mL) was added to each well and incubated for another 4 h. After removing the medium, the purple formazan crystal was dissolved in 150 μL of DMSO. The absorbance of the plates was read at 570 nm by a microplate reader.

In Vitro Transcytosis Studies.

To further investigate the transport of insulin-loaded liposomes across the epithelial cells, the Caco-2 cell monolayer was incubated for 21 days after being seeded on the Transwell plates (Costar). Prior to the studies, the medium was replaced with pre-warmed Hanks' balanced salt solution (HBSS) (pH 6.0) in the apical chamber and HBSS (pH 7.4) in the basolateral chamber and allowed to equilibrate for 1 hour at 37° C. Afterwards, the apical solution was replaced with 200 μL of FITC-insulin+glucose (10 mM), Ins-Liposomes+glucose, Fc-Liposomes+glucose, HA-Fc-Liposomes, HA-Fc-Liposomes+glucose, and HA_CL-Fc-Liposomes+glucose, respectively. After incubation for 2 h at 37° C., the basolateral solution was collected and the amount of transported FITC-insulin was determined using a microplate reader at 519 nm with the excitation wavelength at 495 nm.

In Vivo Absorption.

The animal study protocol was approved by the Institutional Animal Care and Use Committee at North Carolina State University and University of North Carolina at Chapel Hill. STZ-induced adult diabetic mice (male C57B6, Jackson Lab, U.S.A.) were fasted for 6 h before administration. The mice were administered with the following formulations by oral gavage: Fc-Liposomes, HA-Fc-Liposomes, and HA_CL-Fc-Liposomes (4 mL/kg). After 30 min, the experiment group was further orally administered glucose solution (1 g/kg). The mice were euthanized and the duodenum tissue were collected for frozen section after 2 h. Hoechst 33342 was used for nuclei staining, and the cross sections of the tissue were observed by fluorescence microscope.

In Vivo Studies Using Streptozotocin (STZ)-Induced Diabetic Mice.

The in vivo efficacy of glucose-responsive insulin-loaded liposome for diabetes treatment was evaluated on STZ-induced adult diabetic mice (male C57B6, Jackson Lab, U.S.A.). The animal study protocol was approved by the Institutional Animal Care and Use Committee at North Carolina State University and University of North Carolina at Chapel Hill. Mouse glucose levels were monitored for two days before administration, and all mice were fasted for 6 h before administration. Mice (n=5) were chosen per group such that the mean initial blood glucose levels were between 300-500 mg/dL per group. The mice were administered with the following formulation by oral gavage: insulin solution, Fc-Liposomes, HA-Fc-Liposomes, and HA_CL-Fc-Liposomes (insulin dose: 10 U/kg). After 30 min, the experiment group was further orally administered glucose solution (1 g/kg). The glucose levels of each mouse were monitored over time using the Clarity GL2Plus glucose meter (Clarity Diagnostics, Boca Raton, Fla.). The plasma insulin concentration was measured using Invitrogen™ Novex™ EASIA™ Insulin Human ELISA Kit.

Statistical Analysis.

All results presented are Mean±s. d. Statistical analysis was performed using two-tailed Student's t-tests. *P value <0.05 describing the differences between experimental groups and control groups was considered statistically significant.

The compositions and methods of the appended claims are not limited in scope by the specific compositions and methods described herein, which are intended as illustrations of a few aspects of the claims and any compositions and methods that are functionally equivalent are intended to fall within the scope of the claims. Various modifications of the compositions and methods in addition to those shown and described herein are intended to fall within the scope of the appended claims. Further, while only certain representative compositions and method steps disclosed herein are specifically described, other combinations of the compositions and method steps also are intended to fall within the scope of the appended claims, even if not specifically recited. Thus, a combination of steps, elements, components, or constituents may be explicitly mentioned herein or less, however, other combinations of steps, elements, components, and constituents are included, even though not explicitly stated. The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments of the invention and are also disclosed. Other than in the examples, or where otherwise noted, all numbers expressing quantities of ingredients, reaction conditions, and so forth used in the specification and claims are to be understood at the very least, and not as an attempt to limit the application of the doctrine of equivalents to the scope of the claims, to be construed in light of the number of significant digits and ordinary rounding approaches.

What is claimed is:

1. A glucose sensitive drug delivery system comprising a core comprising an active agent and a polymeric shell encapsulating the core, wherein the core is attached to the polymeric shell via a plurality of boronate esters having the structure:

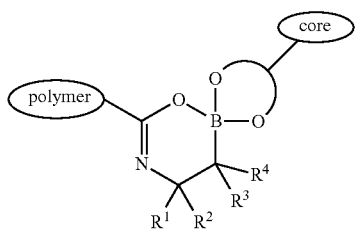

wherein $R^1$, $R^2$, $R^3$, and $R^4$ are independently selected from hydrogen, $C_{1-8}$alkyl, $C_{2-8}$alkenyl, $C_{2-8}$alkynyl, aryl, heteroaryl, $C_{3-8}$cycloalkyl, and $C_{1-8}$heteroaryl, which may be substituted or unsubstituted, and wherein any two or more of $R^1$, $R^2$, $R^3$, and $R^4$ may together form a ring.

2. The drug delivery system of claim 1, wherein $R^1$ and $R^3$ are hydrogen and $R^2$ and $R^4$ together form a phenyl ring.

3. The drug delivery system of claim 1, wherein the polymeric shell comprises a carboxylate-bearing polymer selected from the group consisting of hyaluronic acid, poly (α-glutamic acid), poly(α-glutamic acid), poly(aspartic acid), chondroitin sulfate, carboxymethylcellulose, and combinations thereof, wherein at least a portion of the carboxylate groups are modified to contain the plurality of boronate esters.

4. The drug delivery system of claim 3, wherein the polymeric shell comprises hyaluronic acid.

5. The drug delivery system of claim 3, wherein the core comprises a liposome loaded with a small molecule drug or therapeutic protein.

6. The drug delivery system of claim 1, wherein the active agent comprises as regular insulin, insulin degludec, insulin lispro, insulin aspart, insulin glulisine, insulin detemir, insulin glargine, NPH insulin, animal insulin, or a combination thereof.

7. The drug delivery system of claim 5, wherein the liposome comprises a choline lipid component and an ethanolamine lipid component.

8. The drug delivery system of claim 5, wherein the liposome comprises cholesterol, one or more cholesterol derivatives, or a combination thereof.

9. The drug delivery system of claim 5, wherein the liposome comprises one or more primary lipids selected from phosphatidic acid, phosphatidylcholine, phosphatidylglycerol, phophatidylethanolamine phophatidylinositol, and phosphatidylserine, sphingomyelin, lecithin, lysolecithin, lysophosphatidylethanolamine, cerebrosides, diarachidoylphosphatidylcholine, didecanoyl-L-alpha-phosphatidylcholine, dielaidoylphosphatidylcholine, dilauroylphosphatidylcholine, dilinoleoylphosphatidylcholine, dimyristoylphosphatidylcholine dioleoylphosphatidylcholine, dipalmitoylphosphatidylcholine, distearoylphosphatidylcholine, 1-palmitoyl-2-oleoyl-phosphatidylcholine, diarachidoylphosphatidylglycerol, didecanoyl-L-alpha-phosphatidylglycerol, dielaidoylphosphatidylglycerol, dilauroylphosphatidylglycerol, dilinoleoylphosphatidylglycerol, dimyristoylphosphatidylglycerol, dioleoylphosphatidylglycerol, dipalmitoylphosphatidylglycerol, distearoylphosphatidylglycerol, 1-palmitoyl-2-oleoyl-phosphatidylglycerol, diarachidoylphosphatidylethanolamine, didecanoyl-L-alpha-phosphatidylethanolamine, dielaidoylphosphatidylethanolamine, dilauroylphosphatidylethanolamine, dilinoleoylphosphatidylethanolamine, dimyristoylphosphatidylethanolamine, dioleoylphosphatidylethanolamine, dipalmitoylphosphatidylethanolamine, distearoylphosphatidylethanolamine, 1-palmitoyl-2-oleoyl-phosphatidylethanolamine, diarachidoylphosphatidylinositol, didecanoyl-L-alpha-phosphatidylinositol, dielaidoylphosphatidylinositol, dilauroylphosphatidylinositol, dilinoleoylphosphatidylinositol, dimnyristoylphosphatidylinositol, dioleoylphosphatidylinositol, dipalmitoylphosphatidylinositol, distearoylphosphatidylinositol, 1-palmitoyl-2-olcoyl-phosphatidylinositol, diarachidoylphosphatidylserine, didecanoyl-L-alpha-phosphatidylserine, dielaidoylphosphatidylserine, dilauroylphosphatidylserine, dilinoleoylphosphatidylserine, dimyristoylphosphatidylserine, dioleoylphosphatidylserine, dipalmitoylphosphatidylserine, distearoylphosphatidylserine, 1-palmitoyl-2-olcoyl-phosphatidylserine, diarachidoyl sphingomyelin, didecanoyl sphingomyelin, dielaidoyl sphingomyelin, dilauroyl sphingomyelin, dilinoleoyl sphingomyelin, dimyristoyl sphingomyelin, sphingomyelin, dioleoyl sphingomyelin, dipalmitoyl sphingomyelin, distearoyl sphingomyelin, 1-palmitoyl-2-oleoyl-sphingomyelin, or a combination thereof.

10. The drug delivery system of claim 5, wherein the liposome comprises a polymer anchor bonded to a boronate ester, having the formula:

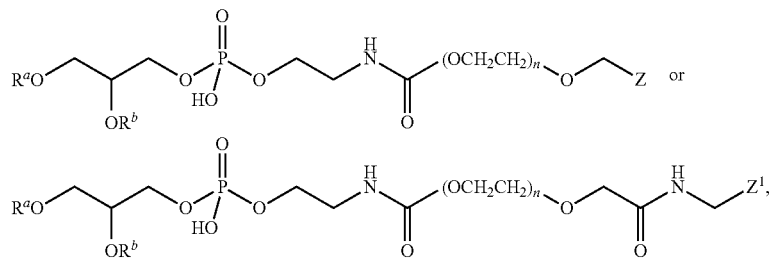

wherein $R^a$ and $R^b$ are independently selected from $C_{6-32}$alkyl-C(O)— or $C_{6-32}$alkenyl-C(O)—, n is an integer from 5-1,000, Z and $Z^1$ are:

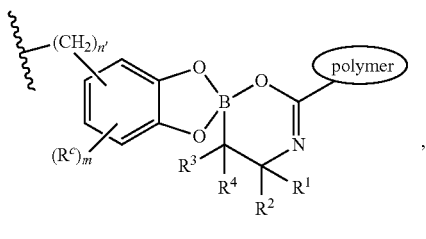

wherein $R^1$, $R^2$, $R^3$, and $R^4$ are independently selected from hydrogen, $C_{1-8}$alkyl, $C_{2-8}$alkenyl, $C_{2-8}$alkynyl, aryl, heteroaryl, $C_{3-8}$cycloalkyl, and $C_{1-8}$heteroaryl, which may be substituted or unsubstituted, and wherein any two or more of $R^1$, $R^2$, $R^3$, and $R^4$ may together form a ring; n' is an integer from 0-10, m is an integer from 0-3, and $R^c$ is independently selected from $R^{c1}$, $OR^{c1}$, $N(R^{c1})_2$, $SiR^{c1}_3$, $SR^{c1}$, $SO_2R^{c1}$, $SO_2N(R^{c1})_2$, $C(O)R^{c1}$; $C(O)OR^{c1}$, $OCOR^{c1}$; $C(O)N(R^{c1})_2$, $OC(O)N(R^{c1})_2$, $N(R^{c1})C(O)N(R^{c1})_2$, F, Cl, Br, I, cyano, and nitro, wherein $R^{c1}$ is in each case independently selected from hydrogen, $C_{1-8}$alkyl, $C_{2-8}$alkenyl, $C_{2-8}$alkynyl, aryl, $C_{1-8}$heteroaryl, $C_{3-8}$cycloalkyl, or $C_{1-8}$heterocyclyl; and wherein any two or more $R^c$ groups may together form a ring.

11. The drug delivery system of claim 5, wherein the liposome comprises a targeting factor.

12. The drug delivery system of claim 11, wherein the targeting factor comprises human IgG Fc fragments, transferrin (Tf), or anti-intercellular adhesion molecule-1 (ICAM-1).

13. The drug delivery system of claim 1, wherein the core is liberated from the polymeric shell in the presence of glucose.

14. A method of treating a hyperglycemic disorder, comprising administering to a patient in need thereof the drug delivery system of claim 6.

15. A method of preparing a drug delivery system, comprising preparing a dry mixture of primary lipids and one or more anchor polymers; combining the dry mixture with an aqueous composition comprising an active agent to provide a liposome; and encapsulating the liposome with a polymer comprising a plurality of boronic esters.

16. The method of claim 15, wherein the anchor polymer has the formula:

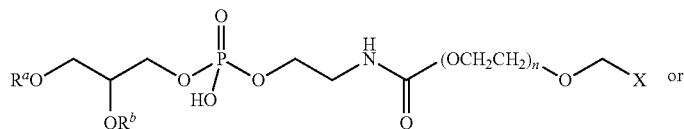

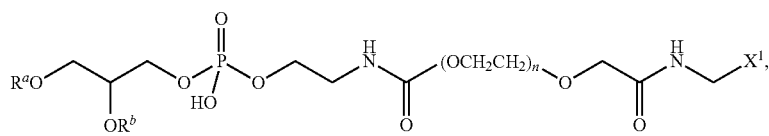

wherein $R^a$ and $R^b$ are independently selected from $C_{6-32}$alkyl-C(O)—, or $C_{6-32}$alkenyl-C(O)—, n is an integer from 5-1,000, and X and $X^1$ are diol bearing group.

17. The method of claim 16, wherein X and $X^1$ are a moiety having the formula:

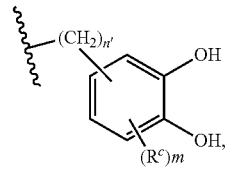

wherein n is an integer from 0-10, m is an integer from 0-3, and $R^c$ is independently selected from $R^{c1}$, $OR^{c1}$, $N(R^{c1})_2$, $SiR^{c1}_3$, $SR^{c1}$, $SO_2R^{c1}$, $SO_2N(R^{c1})_2$, $C(O)R^{c1}$; $C(O)OR^{c1}$, $OCOR^{c1}$; $C(O)N(R^{c1})_2$, $OC(O)N(R^{c1})_2$, $N(R^{c1})C(O)N(R^{c1})_2$, F, Cl, Br, I, cyano, and nitro, wherein $R^{c1}$ is in each case independently selected from hydrogen, $C_{1-8}$alkyl, $C_{2-8}$alkenyl, $C_{2-8}$alkynyl, aryl, $C_{1-8}$heteroaryl, $C_{3-8}$cycloalkyl, or $C_{1-8}$heterocyclyl; and wherein any two or more $R^c$ groups may together form a ring.

18. The method of claim 15, wherein the dry mixture further comprises one or more factor anchors, further comprising the step of conjugating a targeting factor to the factor anchor.

19. The method of claim 15, wherein the polymer comprising a plurality of boronic esters is a hyaluronic acid polymer comprising a plurality of subunits having the structure:

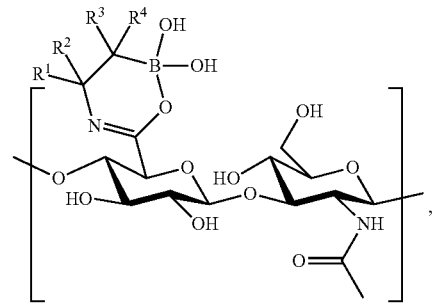

wherein $R^1$, $R^2$, $R^3$, and $R^4$ are independently selected from hydrogen, $C_{1-8}$alkyl, $C_{2-8}$alkenyl, $C_{2-8}$alkynyl, aryl, heteroaryl, $C_{3-8}$cycloalkyl, and $C_{1-8}$heteroaryl, which may be substituted or unsubstituted, and wherein any two or more of $R^1$, $R^2$, $R^3$, and $R^4$ may together form a ring, and unmodified subunits having the structure:
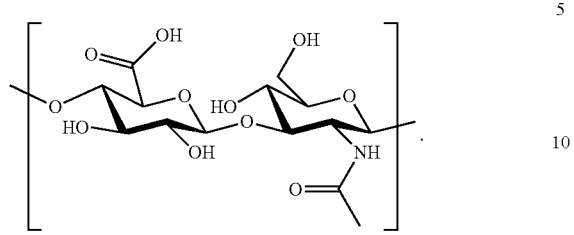
20. A drug delivery system, preparing by the process of claim 15.
* * * * *